(12) United States Patent
Ogasawara et al.

(10) Patent No.: US 11,006,925 B2
(45) Date of Patent: May 18, 2021

(54) PROBE ADAPTER, ULTRASONIC PROBE, AND ULTRASONIC DIAGNOSTIC APPARATUS

(71) Applicant: TOSHIBA MEDICAL SYSTEMS CORPORATION, Otawara (JP)

(72) Inventors: Yoichi Ogasawara, Nasushiobara (JP); Kentaro Tsuzuki, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 756 days.

(21) Appl. No.: 15/592,234

(22) Filed: May 11, 2017

(65) Prior Publication Data

US 2017/0340309 A1  Nov. 30, 2017

(30) Foreign Application Priority Data

May 30, 2016 (JP) .............................. JP2016-107002
Mar. 6, 2017 (JP) .............................. JP2017-041604

(51) Int. Cl.
*A61B 8/00* (2006.01)
*A61B 8/08* (2006.01)
*A61B 8/14* (2006.01)

(52) U.S. Cl.
CPC ............ *A61B 8/4444* (2013.01); *A61B 8/085* (2013.01); *A61B 8/0891* (2013.01); *A61B 8/14* (2013.01); *A61B 8/4254* (2013.01); *A61B 8/4416* (2013.01); *A61B 8/4483* (2013.01); *A61B 8/461* (2013.01); *A61B 8/467* (2013.01)

(58) Field of Classification Search
CPC ....... A61B 8/00; A61B 8/4416; A61B 8/4444; A61B 8/4254; A61B 8/0891; A61B 8/467; A61B 8/4483; A61B 8/461; A61B 8/14; A61B 8/085

USPC .......................................... 398/443, 437, 407
See application file for complete search history.

(56) References Cited

U.S. PATENT DOCUMENTS

| | | | | |
|---|---|---|---|---|
| 3,810,459 A | * | 5/1974 | Becker | A61B 5/103 600/453 |
| 4,010,635 A | * | 3/1977 | Patsey | G01N 29/24 73/644 |
| 4,364,142 A | * | 12/1982 | Pangle | A46B 5/02 119/623 |
| 5,076,279 A | * | 12/1991 | Arenson | A61B 1/00142 600/459 |
| 5,226,419 A | * | 7/1993 | Hanrahan | A61B 90/39 600/437 |
| 5,232,498 A | * | 8/1993 | Hayakawa | A61B 8/4281 118/203 |

(Continued)

FOREIGN PATENT DOCUMENTS

| | | |
|---|---|---|
| JP | 61-8006 U | 1/1986 |
| JP | 5337782 B2 | 11/2013 |

*Primary Examiner* — Oommen Jacob
(74) *Attorney, Agent, or Firm* — Oblon, McClelland, Maier & Neustadt, L.L.P.

(57) ABSTRACT

In one embodiment, a probe adapter includes: a holder configured to be detachably attached to an ultrasonic probe; a marker configured to be disposed at a predetermined position in an array direction of the ultrasonic probe and mark a surface of an object which the ultrasonic probe is brought into contact with, under a state where the holder is attached to the ultrasonic probe; and a wiper configured to remove an ultrasonic medium coated on the surface of an object.

20 Claims, 26 Drawing Sheets

(56) References Cited

U.S. PATENT DOCUMENTS

| | | | | |
|---|---|---|---|---|
| 5,419,195 A * | 5/1995 | Quinn | G01N 29/28 | 73/623 |
| 5,545,942 A * | 8/1996 | Jaster | A61B 8/546 | 174/16.3 |
| 5,617,866 A * | 4/1997 | Marian, Jr. | A61B 8/00 | 600/459 |
| 5,673,996 A * | 10/1997 | Ducker | B43K 29/10 | 362/118 |
| 5,782,767 A * | 7/1998 | Pretlow, III | A61B 8/4281 | 600/443 |
| 5,928,154 A * | 7/1999 | Silber | B25G 1/10 | 600/459 |
| 6,113,559 A * | 9/2000 | Klopotek | A61N 7/00 | 601/3 |
| 6,142,946 A * | 11/2000 | Hwang | G01S 7/52017 | 600/459 |
| 6,190,073 B1 * | 2/2001 | Kabigting | A45D 34/04 | 401/138 |
| 6,203,499 B1 * | 3/2001 | Imling | A61B 8/0833 | 600/461 |
| 6,210,329 B1 * | 4/2001 | Christmas | A61B 50/31 | 600/437 |
| 6,379,307 B1 * | 4/2002 | Filly | A61B 8/0833 | 600/461 |
| 6,530,642 B1 * | 3/2003 | Uchikata | B41J 2/16538 | 347/33 |
| 7,493,154 B2 * | 2/2009 | Bonner | A61B 5/06 | 600/13 |
| 7,865,236 B2 * | 1/2011 | Cory | A61B 5/4041 | 600/547 |
| 8,620,046 B2 * | 12/2013 | Nagler | A61B 6/54 | 382/128 |
| 9,463,630 B2 * | 10/2016 | Thayer | B41J 2/16538 | |
| 10,284,762 B2 * | 5/2019 | Stolka | A61B 34/77 | |
| 2002/0029054 A1 * | 3/2002 | Rabiner | A61B 17/320068 | 606/169 |
| 2002/0103434 A1 * | 8/2002 | Swanbom | A61B 5/6842 | 600/437 |
| 2002/0162185 A1 * | 11/2002 | Wegner | B60S 1/38 | 15/250.48 |
| 2002/0192600 A1 * | 12/2002 | Okamura | B01J 19/0046 | 430/320 |
| 2003/0101532 A1 * | 6/2003 | Desinger | A47L 11/405 | 15/321 |
| 2003/0163147 A1 * | 8/2003 | Rabiner | A61B 17/3415 | 606/159 |
| 2003/0195420 A1 * | 10/2003 | Mendlein | A61B 8/0858 | 600/437 |
| 2004/0082850 A1 * | 4/2004 | Bonner | A61B 5/06 | 600/424 |
| 2005/0033316 A1 * | 2/2005 | Kertz | A61N 7/00 | 606/131 |
| 2005/0101854 A1 * | 5/2005 | Larson | A61L 2/10 | 600/407 |
| 2006/0106312 A1 * | 5/2006 | Farmer | A61B 5/6842 | 600/459 |
| 2007/0116408 A1 * | 5/2007 | Eberle | A61B 1/0017 | 385/31 |
| 2007/0209133 A1 * | 9/2007 | Linzell | A45D 34/04 | 15/209.1 |
| 2007/0225605 A1 * | 9/2007 | Swanbom | A61B 5/6842 | 600/437 |
| 2007/0266778 A1 * | 11/2007 | Corey | A61B 5/15087 | 73/61.75 |
| 2007/0288042 A1 * | 12/2007 | Serbousek | A61B 17/16 | 606/160 |
| 2008/0021317 A1 * | 1/2008 | Sumanaweera | A61B 8/4218 | 600/437 |
| 2008/0021327 A1 * | 1/2008 | El-Bialy | A61N 7/00 | 600/459 |
| 2008/0139944 A1 * | 6/2008 | Weymer | A61B 8/4281 | 600/459 |
| 2008/0194964 A1 * | 8/2008 | Randall | A61B 8/56 | 600/459 |
| 2009/0013493 A1 * | 1/2009 | Park | B60S 1/3808 | 15/250.452 |
| 2009/0199392 A1 * | 8/2009 | Singh | G01H 11/08 | 29/594 |
| 2010/0228124 A1 * | 9/2010 | Brennan | A61B 8/5276 | 600/437 |
| 2011/0184500 A1 * | 7/2011 | Reil | A61N 5/0613 | 607/88 |
| 2011/0271518 A1 * | 11/2011 | Metzger | G01D 11/245 | 29/593 |
| 2013/0186188 A1 * | 7/2013 | Bradley | B08B 3/12 | 73/64.53 |
| 2013/0289381 A1 * | 10/2013 | Oraevsky | A61B 5/14552 | 600/407 |
| 2013/0301380 A1 * | 11/2013 | Oraevsky | A61B 8/5261 | 367/7 |
| 2014/0130621 A1 * | 5/2014 | Palassis | G01D 11/00 | 73/866.5 |
| 2015/0032128 A1 * | 1/2015 | Tavlin | A61N 7/02 | 606/131 |
| 2015/0045645 A1 * | 2/2015 | Eberle | A61B 1/00165 | 600/407 |
| 2015/0173619 A1 * | 6/2015 | Zvuloni | G01B 9/02083 | 600/425 |
| 2016/0022308 A1 * | 1/2016 | Rohling | A61B 8/4411 | 600/424 |
| 2016/0058417 A1 * | 3/2016 | Kiyose | G01S 7/52079 | 600/472 |
| 2017/0340309 A1 * | 11/2017 | Ogasawara | A61B 8/4416 | |

* cited by examiner

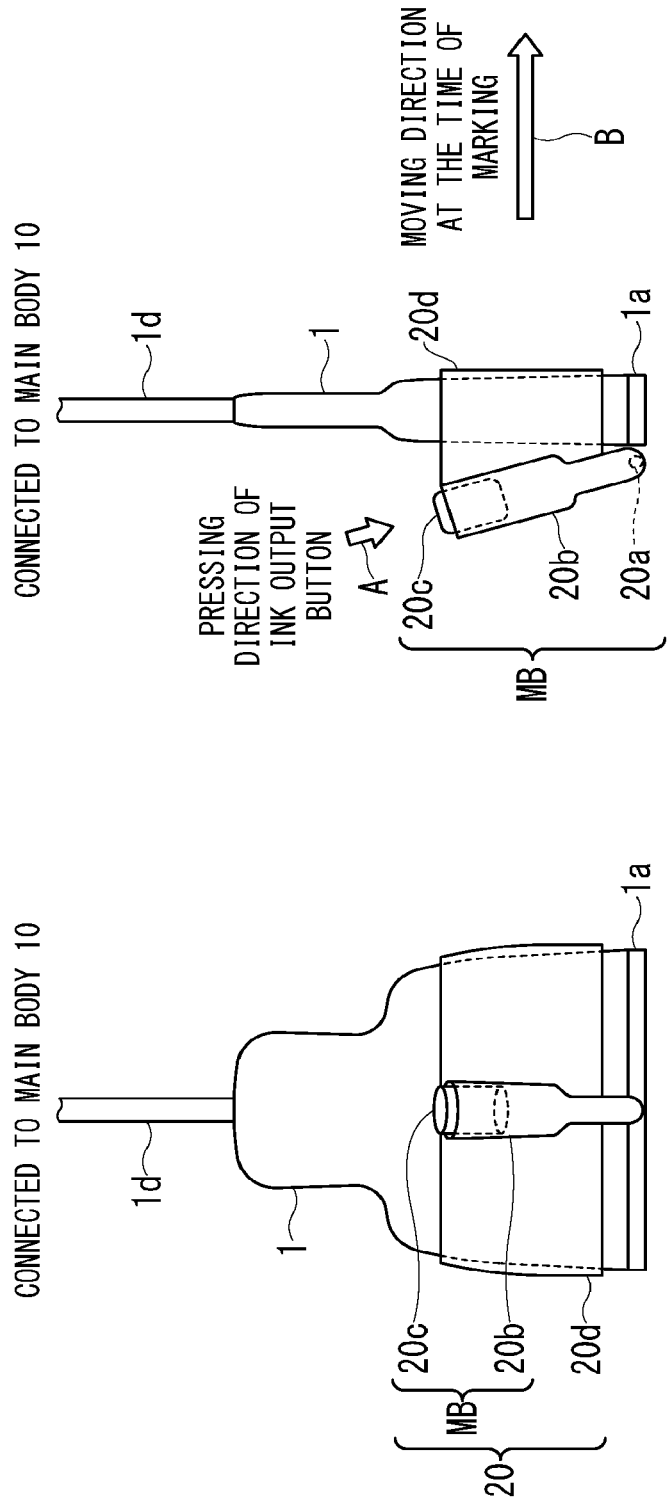
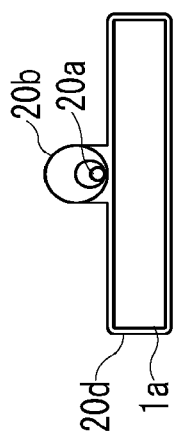
FIG. 6A  FIG. 6B  FIG. 6C

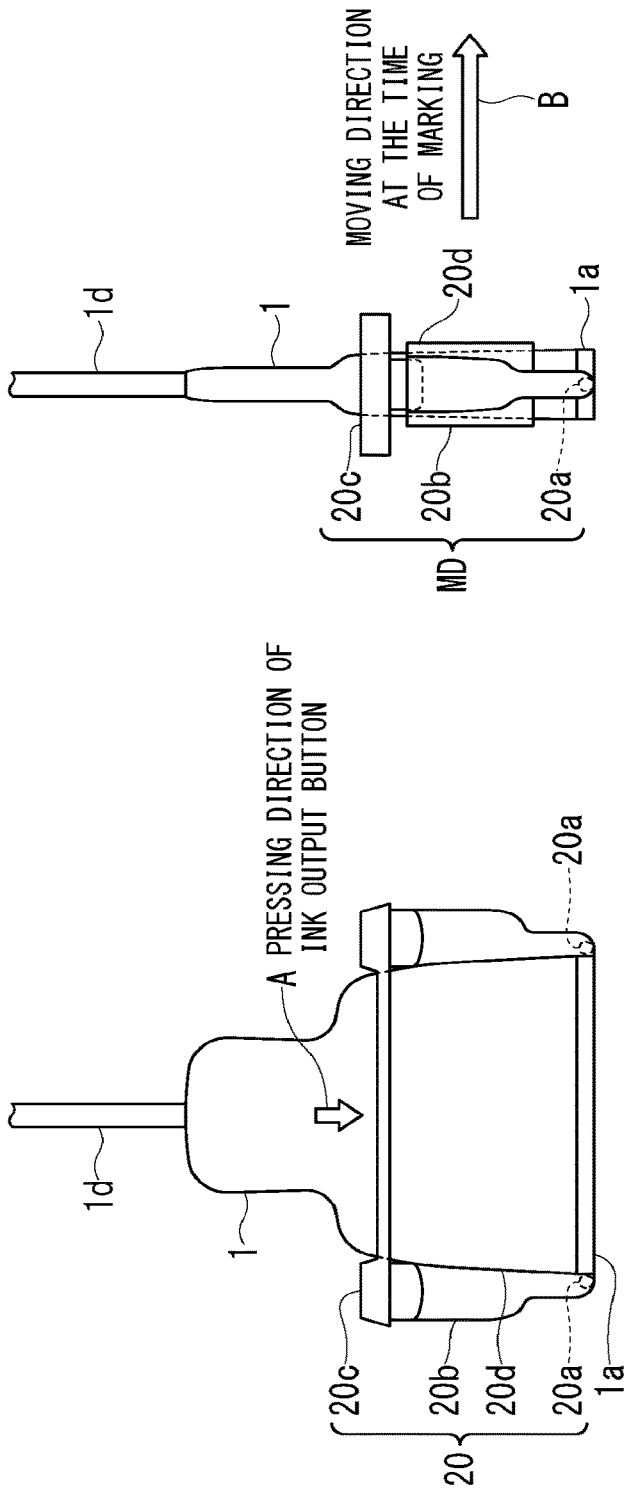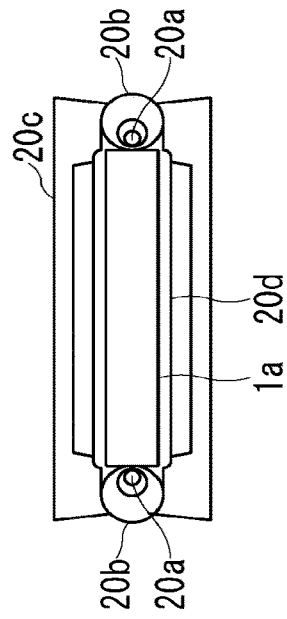

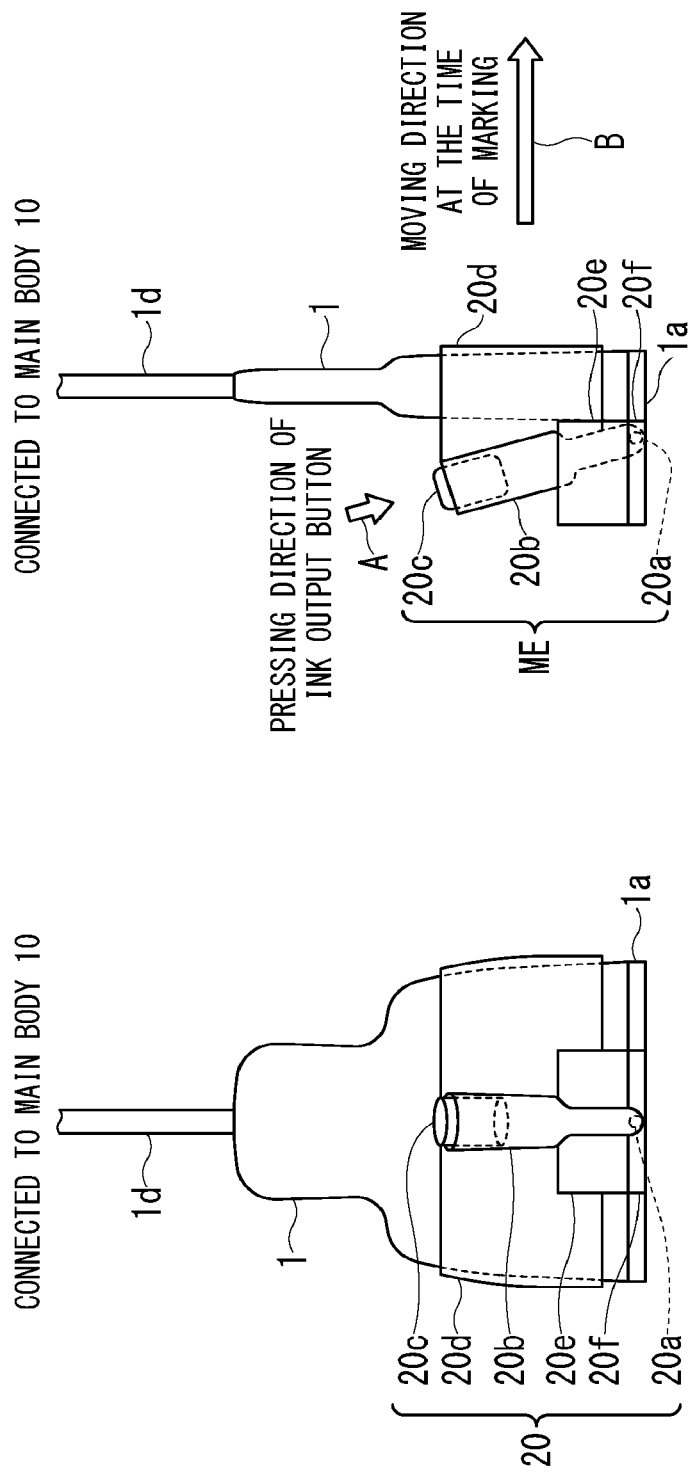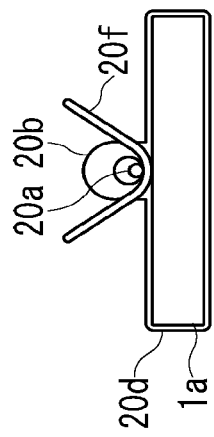

PROBE ADAPTER, ULTRASONIC PROBE, AND ULTRASONIC DIAGNOSTIC APPARATUS

CROSS-REFERENCE TO RELATED APPLICATION

This application is based upon and claims the benefit of priority from Japanese Patent Application No. 2016-107002, filed on May 30, 2016, and Japanese Patent Application No. 2017-41604 filed on Mar. 6, 2017, the entire contents of each of which are incorporated herein by reference.

FIELD

Embodiments described herein relate generally to a probe adapter, an ultrasonic probe, and an ultrasonic diagnostic apparatus.

BACKGROUND

An ultrasonic diagnostic apparatus is configured to non-invasively acquire information inside an object by transmitting an ultrasonic pulse and/or an ultrasonic continuous wave to an object's body and converting the reflected ultrasonic wave into an electric signal with the use of transducers. Note that the reflected ultrasonic wave is generated due to difference in acoustic impedance between respective tissues in the object. In an ultrasonic diagnostic apparatus, transducers are included in an ultrasonic probe, and are controlled such that the transducers transmit an ultrasonic pulse and/or an ultrasonic continuous wave and receive the reflected ultrasonic wave(s).

In a medical examination with the use of an ultrasonic diagnostic apparatus, various type of moving image data and real-time image data can be easily acquired by scanning an object with the ultrasonic probe, i.e., bringing the ultrasonic probe into contact with the surface of the object. Thus, an ultrasonic diagnostic apparatus is widely used for diagnosis of shape and property of an abnormal part such as a tumor and for imaging blood-flow dynamics.

For instance, in a biopsy examination, a living tissue including an abnormal tissue such as a tumor is extracted by using a puncture needle punctured into inside of an object while the inside of the object is being imaged with an ultrasonic diagnostic apparatus on a real-time basis, and the cells included in the extracted living tissue are examined. In a biopsy examination, a puncture position is carefully determined in such a manner that a puncture needle is infallibly punctured into a living tissue including a tumor. Thus, when a biopsy examination is performed, in some cases, a puncture position is determined in advance while a position of a tumor is being observed with an ultrasonic diagnostic apparatus, and then marking is performed on a skin surface of an object with, e.g., a medical marker.

When a tumor is surgically removed aside from a biopsy examination, a tumor position is sometimes marked on a skin surface of an object by preoperative imaging with the use of an ultrasonic diagnostic apparatus. Additionally, in an operation called percutaneous transluminal angioplasty, a running state of blood vessels are sometimes confirmed by imaging with the use of an ultrasonic diagnostic apparatus prior to the operation so that marking indicative of the running state of blood vessels is performed on the skin surface of the object.

Further, as compared with other modalities such as a magnetic resonance imaging apparatus, it is difficult to reproduce imaging of the same region of the same object without marking in the case of an ultrasonic diagnostic apparatus. In imaging with the use of an ultrasonic diagnostic apparatus, it is possible to image the same region again with satisfactory reproducibility by marking a moving trace of an ultrasonic probe on a skin surface of an object. When it is required to display the abnormal part identified in the examination again at the time of the operation, the region to be imaged can be easily reproduced by the marking performed in the examination.

In the above-described case, a user such as a doctor performs marking on a skin surface of an object while imaging inside of the object with manipulating the ultrasonic probe. In this case, when a user performs marking on a target, i.e., a skin surface of an object with a medical marker, the user holds the ultrasonic probe with one hand and holds the medical marker with the other hand so as to perform different manipulations with both hands. When the user performs marking with the non-dominant hand, operability of the ultrasonic probe, marking efficiency, and marking accuracy are reduced.

BRIEF DESCRIPTION OF THE DRAWINGS

In the accompanying drawings:

FIG. 6A, FIG. 6B, and FIG. 6C are plan views illustrating the probe adapter of the second embodiment;

FIG. 10A, FIG. 10B, and FIG. 10C are plan views illustrating the probe adapter of the fifth embodiment;

FIG. 12A, FIG. 12B, and FIG. 12C are plan views illustrating the probe adapter of the sixth embodiment;

DETAILED DESCRIPTION

Hereinafter, descriptions will be given of respective embodiments of probe adapters, ultrasonic probes, and ultrasonic diagnostic apparatuses by referring to the accompanying drawings.

The same reference signs are given for identical components in each figure, and duplicate description is omitted.

In one embodiment, a probe adapter includes: a holder configured to be detachably attached to an ultrasonic probe; a marker configured to be disposed at a predetermined position in an array direction of the ultrasonic probe and mark a surface of an object which the ultrasonic probe is brought into contact with, under a state where the holder is attached to the ultrasonic probe; and a wiper configured to remove an ultrasonic medium coated on the surface of the object.

First Embodiment

The first embodiment relates to an ultrasonic probe equipped with a marker for marking a skin surface of an object and also relates to an ultrasonic diagnostic apparatus equipped with such an ultrasonic probe.

Figure 1:
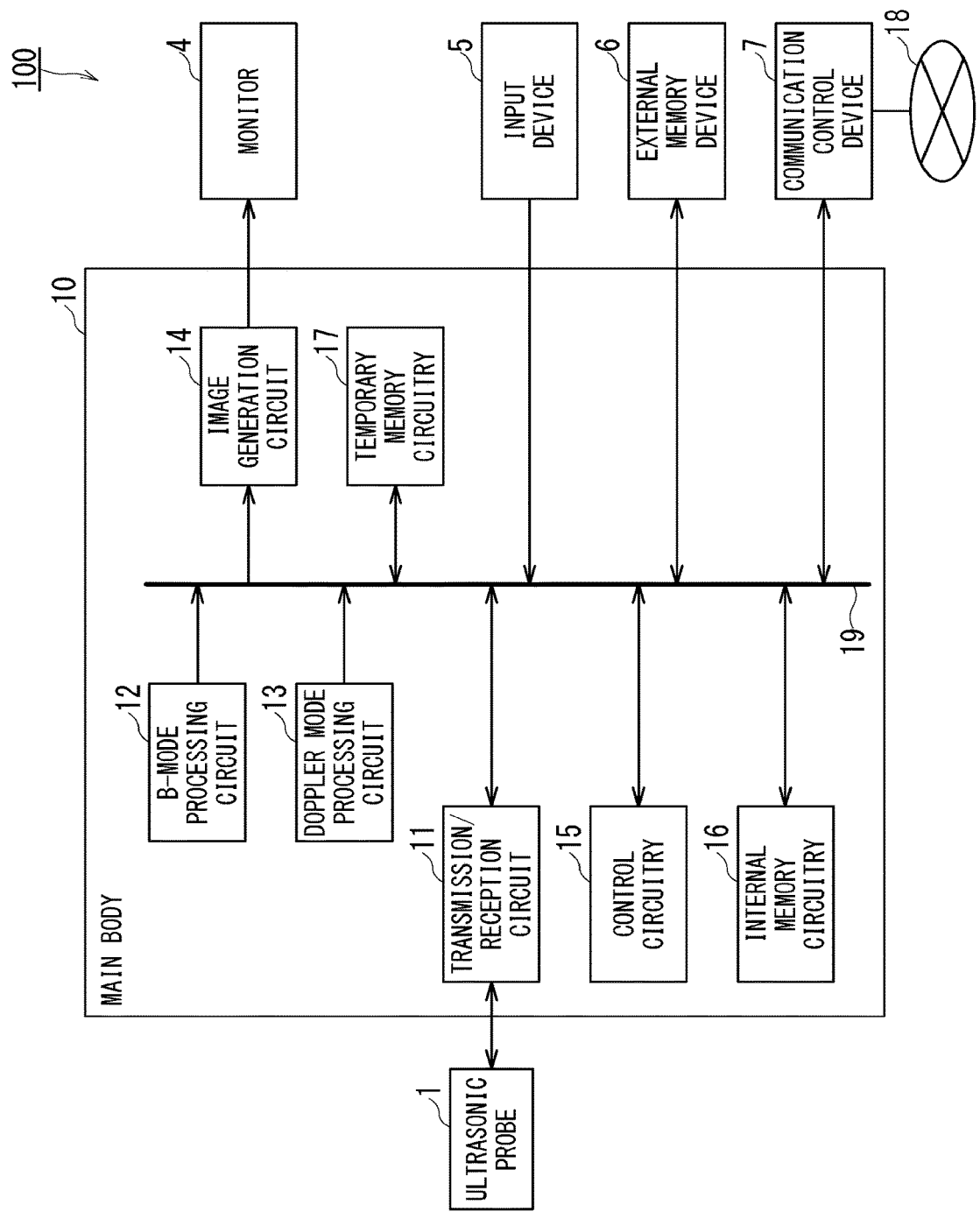
FIG. 1 is a general block diagram illustrating configuration of the ultrasonic diagnostic apparatus of the first embodiment.

FIG. 1 is a general block diagram illustrating the configuration of the ultrasonic diagnostic apparatus 100 of the first embodiment. The ultrasonic diagnostic apparatus 100 includes an ultrasonic probe 1, a main body 10, a monitor 4, an input device 5, external memory device 6, and a communication control device 7.

The ultrasonic probe 1 is equipped with plural transducers. These transducers convert a transmission wave, which is outputted as an electric signal from the main body 10, into an ultrasonic transmission wave, and transmit the ultrasonic transmission wave to an object. Additionally, the transducers convert an ultrasonic signal reflected from the object into a reception signal as an electric signal, and outputs this reception signal to the main body 10. The ultrasonic probe 1 can be attachably/detachably connected to the main body 10 with a probe cable and a connecter.

The ultrasonic probe 1 of the first embodiment further includes a marker (not shown in FIG. 1). The marker performs marking on a skin surface of an object by using, e.g., ink for skin and/or a skin sticking material which includes an adhesive agent and sticks to a skin of an object. The ultrasonic probe 1 equipped with the marker will be described below in detail by referring to FIG. 2A, FIG. 2B, FIG. 2C, and FIG. 3.

The ultrasonic probe 1 may be a one-dimensional array probe in which plural transducers are linearly arrayed or a two-dimensional array probe in which plural transducers are two-dimensionally arrayed. Additionally, the ultrasonic probe 1 may be a probe of mechanical scan type whose transducers are mechanically moved by, e.g., driving a motor. For instance, the ultrasonic probe 1 may be a mechanical probe which acquires information inside a living body in three-dimensional space by driving a motor so as to mechanically fluctuate its one-dimensional array structure of linearly-arrayed transducers in the direction perpendicular to the array direction.

The monitor 4 is a display configured of, e.g., a liquid crystal panel. The monitor 4 displays various types of ultrasonic images generated by an image generation circuit 14 in addition to data and information related to a user interface.

The input device 5 is an operation device for a user such as a keyboard, a mouse, a joystick, and a track ball. When the monitor 4 is equipped with a touch panel, this touch panel is included in the input device 5.

The external memory device 6 is configured of, e.g., a hard disc, an optical disc, or a semiconductor memory element such as a RAM (Random Access Memory) and a flash memory. The external memory device 6 may be configured as circuitry to which a portable media such as a USB (Universal Serial Bus) memory and a DVD (Digital Video Disk) can be attachably/detachably connected.

The communication control device 7 implements various types of communication protocols according to a network aspect. The above-described electronic network 18 means the entire information communication network using telecommunications technology, and includes, e.g., a telephone communication network, an optical fiber communication network, a cable communication network, and a satellite communication network in addition to a hospital LAN (Local Area Network), a wireless/wired LAN, and the Internet network. The ultrasonic diagnostic apparatus 100 can transmit and receive image data from/to the external memory device 6 such as an image server via the electronic network 18.

The main body 10 includes a transmission/reception circuit 11, a B-mode processing circuit 12, a Doppler mode processing circuit 13, the above-described image generation circuit 14, control circuitry 15, internal memory circuitry 16, and temporary memory circuitry 17. The control circuitry 15 is interconnected with respective hardware components constituting the main body 10 via a bus as a transmission path of common signals.

The transmission/reception circuit 11 generates a transmission wave, then amplifies the transmission wave to a predetermined voltage, and then supplies the amplified transmission wave to the respective transducers.

Additionally, the transmission/reception circuit 11 generates a reception signal on the basis of a reflected wave which is reflected from an object and detected by the respective transducers. The transmission/reception circuit 11 includes a preamplifier, an analogue/digital converter, a reception delay circuit, and an adder (not shown).

The preamplifier amplifies reception signals outputted from the respective transducers of the ultrasonic probe 1 to a predetermined voltage. The analogue/digital converter converts each of the amplified reception signals into digital amount. The reception delay circuit delays the digitized reception signals by delay amounts which are different for each transducer. Each delay amount is computed on the basis of information such as a reception focus position and/or a scanning direction of a reception ultrasonic beam instructed by the control circuitry 15. The adder performs phase-compensation/summation (phase-matching addition) on the respective reception signals delayed by delay amounts which are different for each transducer. The reception signals subjected to phase-compensation/summation is referred to as scan-line data.

Since the reception delay circuit and the adder form a reception beam oriented to a predetermined direction, the reception delay circuit and the adder are collectively referred to as a beam former in some cases. Additionally, output signals from the adder can also be referred to as reception signals received by the formed reception beam.

The B-mode processing circuit 12 is a circuit configured to operate when the ultrasonic diagnostic apparatus 100 is set to the B-mode, and acquires amplitude information of a reflected wave by performing signal processing such as amplitude detection and logarithmic compression on scan-line data.

The Doppler mode processing circuit 13 is a circuit configured to operate when the ultrasonic diagnostic apparatus 100 is set to the Doppler mode. The Doppler mode processing circuit 13 acquires velocity information of fluid such as blood in a designated direction and at a designated position by performing signal processing such as Fourier transform on scan-line data. In particular, in the color Doppler mode, the Doppler mode processing circuit 13 acquires power information and information on an average value and variance of fluid velocity (e.g., blood flow velocity) in addition to the velocity information of fluid by performing signal processing such as MTI (Moving Target Indicator) filter and autocorrelation on the reception signals.

Scan-line data which are subjected to image processing by the B-mode processing circuit 12 or the Doppler mode processing circuit 13 are referred to as frame data. Frame data are temporarily stored in, e.g., a frame storage region in the temporary memory circuitry 17. The frame storage region may be provided in the internal memory circuitry 16 or a circuit dedicated to storage of frame data may be separately provided.

The image generation circuit 14 performs scan conversion on the frame data, which have been subjected to image processing depending on an operation mode such as the B-mode and the Doppler mode, according to a beam direction and distance (depth). The image generation circuit 14 generates data for display on the monitor 4, i.e., an ultrasonic image by performing predetermined image processing on the frame data subjected to the scan conversion.

When the original data for generating one ultrasonic image are defined as one set of frame data, plural sets of frame data are time-sequentially generated in such a manner that set number of frame data to be generated is in accordance with the designated frame rate. Thus, the image generation circuit 14 updates an ultrasonic image displayed on the monitor 4 in real-time by performing image processing on predetermined set number of frame data per unit time, which predetermined set number is in accordance with the frame rate.

The control circuitry 15 is equipped with a processor, and controls the entirety of the main body 10 by causing the processor to execute predetermined programs stored in the internal memory circuitry 16.

The above-described term "processor" means, e.g., a circuit such as a special-purpose or general-purpose central processing unit (CPU), a special-purpose or general-purpose graphics processing unit (GPU), an application specific integrated circuit (ASIC), a programmable logic device, and a field programmable gate array (FPGA). The above-described programmable logic device includes, e.g., a simple programmable logic device (SPLD) and a complex programmable logic device (CPLD). The control circuitry 15 implements various types of functions by reading out programs stored in the internal memory circuitry 16 and executing the programs. Additionally or alternatively, the control circuitry 15 implements various types of functions by reading out programs stored in its own processer and executing the programs.

Further, the control circuitry 15 may be configured of a single processor or may be configured of a combination of plural processors which are independent of each other. In the latter case, plural memory circuits may be provided for the respective processors so that programs executed by each processor are stored in the memory circuit provided for this processor. As a further modification, one memory circuit may collectively store all the programs corresponding to the respective functions of the plural processors.

Each of the internal memory circuitry 16 and the temporary memory circuitry 17 is configured of, e.g., a hard disc, an optical disc, or a semiconductor memory element such as a RAM and a flash memory.

The internal memory circuitry 16 stores image data and data which are necessary for the control circuitry 15 to execute various types of programs.

Next, a description will be given of the ultrasonic probe 1 equipped with the marker in the first embodiment by referring to FIG. 2A, FIG. 2B, and FIG. 2C, and FIG. 3.

Figure 2A:
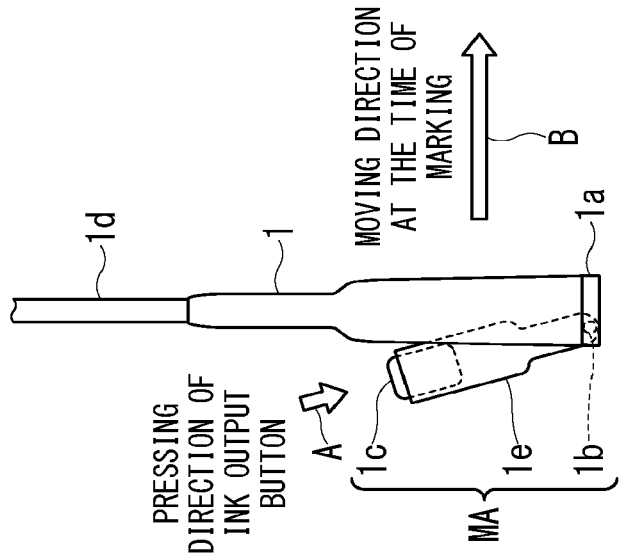
FIG. 2A, FIG. 2B, and FIG. 2C are plan views illustrating the ultrasonic probe of the first embodiment.
Figure 2B:
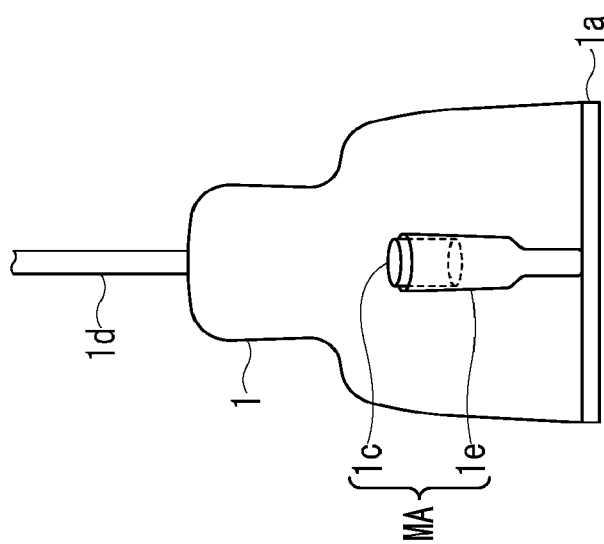
Figure 2C:
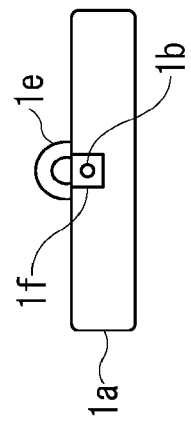

FIG. 2A, FIG. 2B, and FIG. 2C are plan views illustrating the ultrasonic probe 1 of the first embodiment. Specifically, FIG. 2A is a front view, FIG. 2B is a side view, and FIG. 2C is a bottom view. As an example here, out of the respective surfaces of the ultrasonic probe 1 which are approximately perpendicular to its bottom surface to be brought into contact with the object, the mounting plane of the marker MA is defined as the front surface of the ultrasonic probe 1 as shown in FIG. 2A (except a case of being equipped with plural markers like the fifth embodiment). Additionally, out of the respective surfaces of the ultrasonic probe 1 which are approximately perpendicular to its bottom surface, both sides of the front surface are respectively defined as the right surface and the left surface of the ultrasonic probe 1. FIG. 2B illustrates the right surface of the ultrasonic probe 1. Incidentally, the ultrasonic probe 1 shown in FIG. 2A, FIG. 2B, and FIG. 2C is an example of a one-dimensional array probe in which plural transducers are linearly arranged.

The marker MA of the ultrasonic probe 1 shown in FIG. 2A is equipped with a button 1c and an ink tank 1e. The ultrasonic probe 1 is connected to the main body 1 via the probe cable 1d. A probe head 1a is the bottom surface of the ultrasonic probe 1 to be brought into contact with a skin surface of an object, and is made of flexible material such as silicone in order to protect the skin of the object.

In the case of FIG. 2A, the marker MA is integrally provided on the center of the front surface of the ultrasonic probe 1.

As shown in FIG. 2B, an ink ejection port 1b is provided on the same surface as the probe head 1a so as to be in contact with a skin surface of an object. Since the marker MA is configured as described above, when the button 1c is pressed into inside of the marker MA in the direction indicated by the arrow A in FIG. 2B, the pressure inside the ink tank 1e is increased and the ink is applied (coated) from the ink ejection port 1b to a skin surface of an object. The arrow B in FIG. 2B indicates the moving direction of the ultrasonic probe 1 at the time of marking. A user such as a doctor can apply ink on a skin surface of an object by pressing down the button 1c at a position where the user hopes to mark while sliding the ultrasonic probe 1 in the direction of the arrow B.

Note that FIG. 2A, FIG. 2B, and FIG. 2C illustrate a case where the button 1c is disposed at the upper part of the ink tank 1e. However, it is sufficient that the button 1c is provided on the ink tank 1e, and the position of the button 1c is not limited to the case shown in FIG. 2A to FIG. 2C. For instance, the button 1c may be disposed at a position where a user can easily press the button 1c while holding and operating the ultrasonic probe 1 with the hand. Although FIG. 2B illustrates a case where the ink tank 1e is provided so as to be protruded from the ultrasonic probe 1, the ink tank 1e may be housed in the housing of the ultrasonic probe 1 so that the button 1c is provided on the surface of this housing.

As shown in FIG. 2C, the ink ejection port 1b is disposed on the surface of the probe head 1a so as to be brought into contact with a skin surface of an object. FIG. 2C illustrates a case where a cutout region (i.e., notch region or hole) 1f is formed on a part of the probe head 1a in order for the ink ejection port 1b to be brought into contact with a skin surface of an object.

Figure 3:
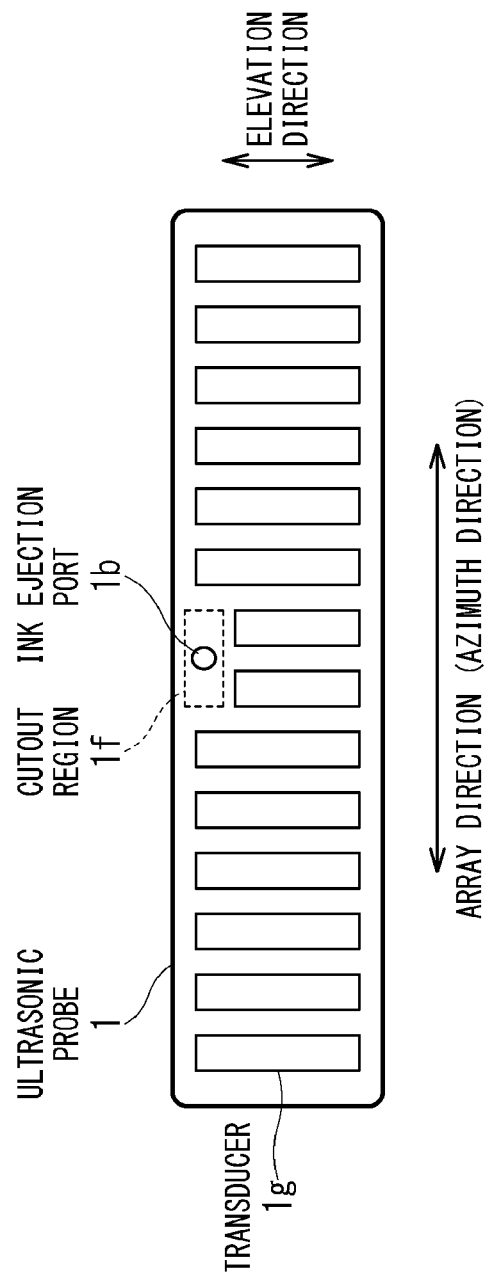
FIG. 3 is a schematic diagram illustrating a row of transducers included in the ultrasonic probe of the first embodiment.

FIG. 3 is a schematic diagram illustrating a row of transducers included in the ultrasonic probe 1 of the first embodiment. FIG. 3 is a schematic bottom view of the ultrasonic probe 1 when the array of the transducers of the ultrasonic probe 1 in the first embodiment is viewed from the side of the probe head 1a.

In the housing of the ultrasonic probe 1, plural transducers 1g are arrayed in the array direction (i.e., azimuth direction). In the case of FIG. 3, fourteen transducers 1g are arrayed in the array direction, and the central two of those fourteen transducers 1g are shorter than the other twelve transducers 1g in the direction perpendicular to the array direction by an extent which has no influence on image quality. This configuration is one of the characteristics of the first embodiment, and allows the ultrasonic probe 1 to have the cutout region 1f indicated by the dashed-line frame in FIG. 3. In the first embodiment, the ultrasonic probe 1 as an imaging structure and the marking structure are successfully integrated by this revolutionary configuration of providing the ink ejection port 1b within the cutout region 1f. According to this revolutionary configuration, it is possible to mark a skin surface which is an outer edge of a cross-section of an object to be observed in an ultrasonic image on a real-time basis.

Figure 4:
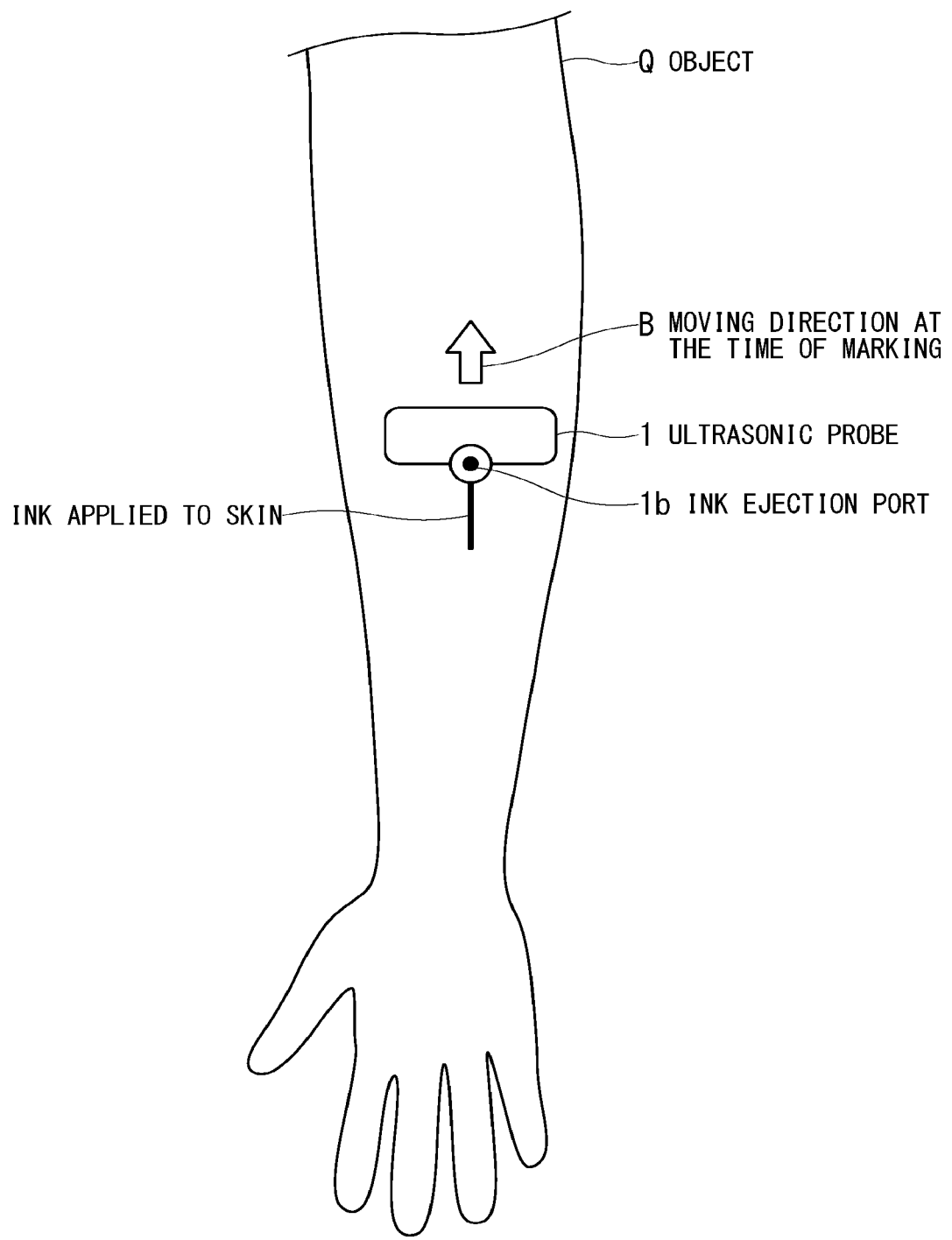
FIG. 4 is a schematic diagram illustrating a case of using the ultrasonic probe of the first embodiment.

FIG. 4 is a schematic diagram illustrating a case of using the ultrasonic probe 1 of the first embodiment. FIG. 4 illustrates a case where the ultrasonic probe 1 is moved on the skin surface of the arm of the object Q in the direction of the arrow B. For instance, when the ultrasonic probe 1 is moved toward the upper arm side in the direction of the arrow B in FIG. 4, i.e., in the direction from the lower side to the upper side on the sheet of FIG. 4, ink is applied to the skin surface of the object Q from the ink ejection port 1b in accordance with this movement of the ultrasonic probe 1. As shown FIG. 4, the ink applied from the ink ejection port b1 becomes a trace of movement of the ink ejection port 1b provided on the center of the front surface of the ultrasonic probe 1. In this manner, a trace of movement of the ultrasonic probe 1 is marked on the skin surface of the arm of the object Q.

For instance, when a blood vessel in the arm of the object Q is observed in the short-axis direction, the ultrasonic probe 1 is brought into contact with the skin surface of the object Q in such a manner that the array direction becomes perpendicular to the running direction of this target blood vessel as shown in FIG. 4. In imaging of a blood vessel in the short-axis direction, shape and size of a cross-section of a blood vessel can be observed. In observation of a blood vessel in the short-axis direction, for instance, the ultrasonic diagnostic apparatus 100 computes the area of the narrowest cross-section of this blood vessel narrowed by stenosis. By marking the position on the skin surface which is the narrowest cross-section of the blood vessel, it is possible to indicate where the stenosis region exists on the arm of the object Q.

As one case of methods of operating the ultrasonic probe 1, a user can simultaneously perform both of marking work and movement of the ultrasonic probe 1 by pressing down the button 1c with the thumb of the dominant hand, while gripping and sequentially moving the ultrasonic probe 1 with the four fingers of the dominant hand. This manipulation can be performed with one hand without difficulty.

According to the ultrasonic diagnostic apparatus 100 equipped with the ultrasonic probe 1 of the first embodiment as described above, a user can perform both of movement of the ultrasonic probe 1 and marking work on a skin surface of an object with one hand without difficulty. Additionally, the configuration of the first embodiment is advantageous in moving the ultrasonic probe 1 in the elevation direction.

Although a description has been given of the case where ink is used as a marking means, a marking means is not limited to ink. For instance, the ultrasonic probe 1 may be configured to mark by using another marking means such as a sticking material coated with an adhesive agent on its one side and another sticking material whose adhesive property is activated by water and/or ultrasonic jelly.

Additionally, though a description has been given of the case where the marker MA is integrally provided on the ultrasonic probe 1 in the first embodiment, the marker MA may be detachably attached to the ultrasonic probe 1. For instance, in the case shown in FIG. 2A to FIG. 2C, the ultrasonic probe 1 may be configured such that the ultrasonic probe 1 can be used in the state of removing the marker MA. Additionally, a part of the marker MA may be configured to be detachable. In other words, the button 1c and the ink tank 1e may be configured to be detachable from the marker MA. When the marker MA is configured to be detachable from the ultrasonic probe 1 as described above, it is easy to perform maintenance such as cleaning and sterilization.

Second Embodiment

The second embodiment relates to an ultrasonic diagnostic apparatus configured to include a probe adapter equipped with a marker for marking a skin surface of an object and an ultrasonic probe to which this probe adapter is attached.

Figure 5:
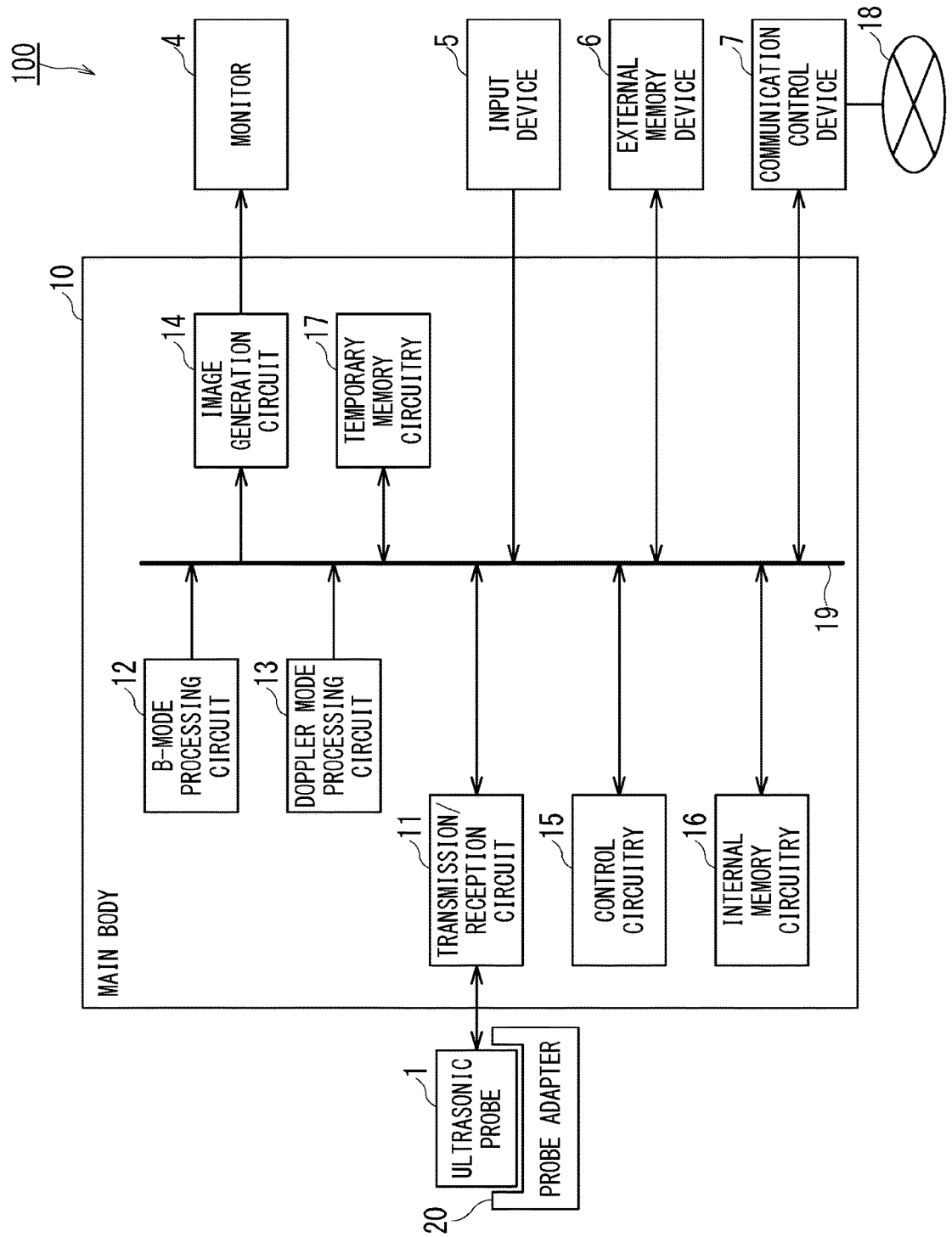
FIG. 5 is a general block diagram illustrating configuration of the ultrasonic diagnostic apparatus of the second embodiment.

FIG. 5 is a general block diagram illustrating configuration of the ultrasonic diagnostic apparatus 100 of the second embodiment. The difference between the first and second embodiments lies in that the ultrasonic diagnostic apparatus 100 of the second embodiment includes the ultrasonic probe 1 and further includes a probe adapter 20 equipped with a marker for marking as a component independent of the ultrasonic probe 1. The probe adapter 20 is detachably attached to the ultrasonic probe 1.

FIG. 6A, FIG. 6B, and FIG. 6C are plan views illustrating the probe adapter 20 of the second embodiment. FIG. 6A is a front view of the ultrasonic probe 1 to which the probe adapter 20 is attached, FIG. 6B is a side view of the ultrasonic probe 1 to which the probe adapter 20 is attached, FIG. 6C is a bottom view of the ultrasonic probe 1 to which the probe adapter 20 is attached.

As shown in FIG. 6A, the probe adapter 20 includes a holder 20d for being attached to (or being mounted on) the ultrasonic probe 1 and the marker MB for marking a skin surface of an object. The marker MB includes the ink ejection port 1a, the ink tank 20b, and the button 20c in a manner similar to the first embodiment. FIG. 6A illustrates a case where the marker MB is disposed at the center of the ultrasonic probe 1 in the array direction.

Although FIG. 6A and FIG. 6B illustrate a case where the button 20c is provided at the upper part of the ink tank 20b in a manner similar to the first embodiment, the position of the button 20c is not limited as long as the button 20c is provided near the ink tank 20b.

Additionally, though FIG. 6A, FIG. 6B, and FIG. 6C illustrate a case where the ink tank 20b is protruded from the adapter 20 and is provided as a pen-shaped structure in a manner similar to FIG. 2A, FIG. 2B, and FIG. 2C, the shape of the ink tank 20b is not limited to the shape shown in FIG. 6A to FIG. 6C. For instance, the holder 20d and the ink tank 20b may be integrally formed.

Since the marker MB is configured as described above, when the button 20c is pressed into inside of the marker MB in the direction of the arrow A in FIG. 6B, the pressure inside the ink tank 20b is increased and thus ink is applied from the ink ejection port 20a to a skin surface of an object. The arrow B in FIG. 6B indicates the moving direction of the ultrasonic probe 1 at the time of marking. A user such as a doctor can apply ink to a skin surface of an object by pressing down the button 20c at a position to be marked, while sliding the ultrasonic probe 1 in the direction of the arrow B.

As shown in FIG. 6C, the ink ejection port 20a is provided along the outer edge of the probe head 1a so as to be brought into contact with a skin surface of an object.

Additionally, the position of the marker MB is not limited to the center on the front surface of the ultrasonic probe 1 under the state where the probe adapter 20 is attached to the ultrasonic probe 1, but the marker MB may be movably (rotatably or slidably) mounted on the holder 20d. For instance, the marker MB may be slidably mounted on the probe adapter 20 in such a manner that the ink ejection port 20a can be moved on the surface that is in parallel with a skin surface of an object. For instance, when a tumor inside a liver is observed from underneath ribs, in some cases, the ultrasonic probe 1 cannot be moved to the position of the tumor due to existence of the ribs. The probe adapter 20 may be configured so that only the marker MB can be manually slid and can mark the position of the tumor even in such cases. Further, the marker MB may be configured to be electrically slid.

As described above, in the ultrasonic diagnostic apparatus 100 of the second embodiment, the same effects as the first embodiment can also be obtained.

Additionally, in the ultrasonic diagnostic apparatus 100 of the second embodiment, it is easy to attach and detach the probe adapter 20 to/from the ultrasonic probe 1. Further, by using elastic material such as silicon and rubber for the holder 20d of the probe adapter 20, the probe adapter 20 can be detachably attached to the ultrasonic probe 1 regardless of the shape of this ultrasonic probe 1. Moreover, even when an ultrasonic diagnostic apparatus is a conventional product, the above-described effects can be obtained only by attaching the probe adapter 20 of the second embodiment to a conventional ultrasonic probe, and thus manufacturing cost can be reduced.

Although a description has been given of the case where the holder 20d is in the form of covering all the side surfaces of the ultrasonic probe 1 in FIG. 6A, FIG. 6B, and FIG. 6C, shape and material of the holder 20d are not limited to the above-described shape and material as long as the probe adapter 20 is in the form of being steadily (firmly) attached to the ultrasonic probe 1. For instance, the holder 20d may be in the form of pinching both side surfaces of the ultrasonic probe 1.

Third Embodiment

The third embodiment relates to an ultrasonic diagnostic apparatus configured to include a probe adapter equipped with a marker for marking a body surface of an object and an ultrasonic probe to which this probe adapter is attached, similarly to the second embodiment.

In the ultrasonic diagnostic apparatus 100 of the third embodiment, the probe adapter 20 includes a medical marking pen 30 as a marker instead of the ink ejection port 1b, the ink tank 1e, and the button 20c in the second embodiment. The marking pen 30 is detachably attached to the holder 20d. Hereinafter, a description will be given of the difference between the second and third embodiments, and duplicate description will be omitted.

Figure 7A:
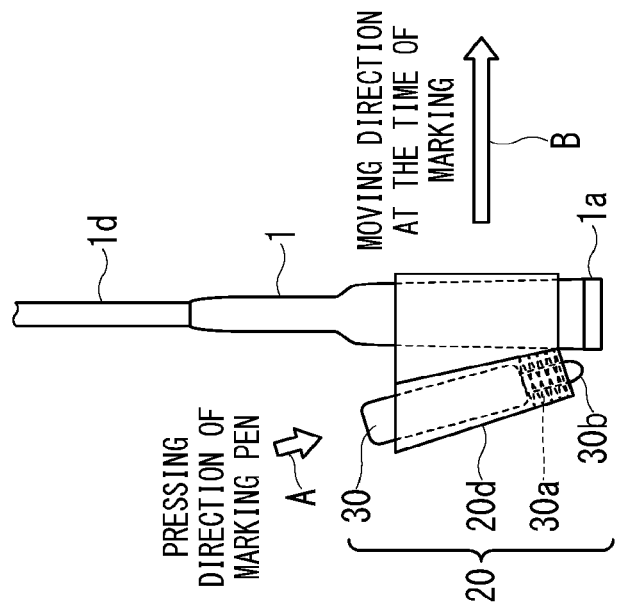
FIG. 7A, FIG. 7B, and FIG. 7C are plan views illustrating the probe adapter of the third embodiment.
Figure 7B:
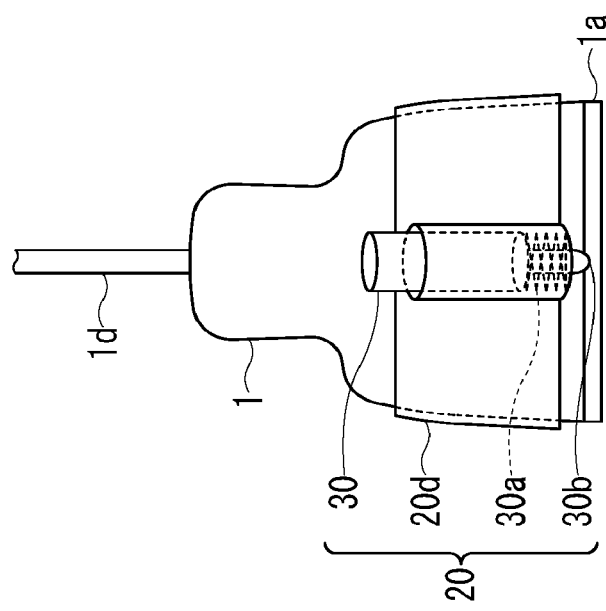
Figure 7C:
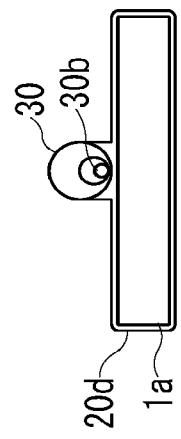

FIG. 7A, FIG. 7B, and FIG. 7C are plan views illustrating the probe adapter 20 of the third embodiment. FIG. 7A is a front view of the ultrasonic probe 1 to which the probe adapter 20 is attached, FIG. 7B is a side view of the ultrasonic probe 1 to which the probe adapter 20 is attached, and FIG. 7C is a bottom view of the ultrasonic probe 1 to which the probe adapter 20 is attached.

In the ultrasonic diagnostic apparatus 100 of the third embodiment as shown in FIG. 7A, FIG. 7B, and FIG. 7C, the probe adapter 20 differs from the second embodiment in that the probe adapter 20 includes the marking pen 30 as a marking means instead of ink. FIG. 7A, FIG. 7B, and FIG. 7C illustrate a case where the marking pen 30 is provided at the center of the front surface of the ultrasonic probe 1. The holder 20d is disposed so as to support the marking pen 30. In the case of FIG. 7A, FIG. 7B, and FIG. 7C, a cylindrical structure capable of holding the marking pen 30 is provided on the holder 20d, and this cylindrical structure allows the marking pen 30 to become detachable in the direction perpendicular to the array direction.

The marking pen 30 shown in FIG. 7A includes an adjuster 30a configured of an elastic body such as a spring, on the side of its pen tip 30b. The adjuster 30a is disposed inside the cylindrical structure capable of holding the marking pen 30. When marking is performed on a skin surface of an object, the adjuster 30a adjusts the position of the tip 30b of the marking pen 30 such that the tip of the marking pen 30 is brought into contact with the skin surface of the object. When marking is not performed, the adjuster 30a adjusts the position of the marking pen 30 such that the tip 30b of the marking pen 30 is separated from a skin surface of an object.

For instance, when the marking pen 30 is pressed into inside of the cylindrical structure in the direction of the arrow A in FIG. 7B, the tip 30 of the marking pen 30 is brought into contact with a skin surface of an object by the adjuster 30a. When press of the marking pen 30 is stopped, the tip 30 of the marking pen 30 is separated from a skin surface of an object by the adjuster 30a.

As shown in FIG. 7C, the tip 30 of the marking pen 30 is provided along the outer edge of the probe head 1a so as to be brought into contact with a skin surface of an object.

Although a description has been given of the case where the marking pen 30 is positioned at the front surface of the ultrasonic probe 1, the marking pen 30 may be slidably mounted on the probe adapter 20 such that the tip 30b of the marking pen 30 can be moved on a plane which is in parallel with a skin surface of an object. Additionally, the marking pen 30 may be configured to be manually slid or be electrically slid.

Further, the adjuster 30a may be configured such that the tip 30b of the marking pen 30 is fixed in the state of being in contact with a skin surface of an object when the marking pen 30 is pressed in the direction of the arrow A in FIG. 7B.

Moreover, the adjuster 30a may be configured such that the tip 30b of the marking pen 30 is separated from a skin surface of an object at the time of pressing the marking pen 30 again in the direction of the arrow A under the state where the tip 30b of the marking pen 30 is in contact with the skin surface of the object.

As described above, in the ultrasonic diagnostic apparatus 100 of the third embodiment, the same effects as the first embodiment can also be obtained. Additionally, in the third embodiment, since the probe adapter 20 is equipped with the adjuster 30a, it is possible to adjust the marking pen 30 in such a manner that the marking pen 30 is brought into contact with a skin surface only at the time of marking. Further, since the marking pen 30 is used for a marking means, color of ink and line width to be drawn by the tip 30b can be easily changed. Moreover, since a disposable marking pen can be used for the probe adapter 20 of the third embodiment, the probe adapter 20 of the third embodiment can be conveniently used under a condition where it is required to use satisfactorily sterilized tools or instruments like a surgical operation.

Fourth Embodiment

Although descriptions have been given of the cases where the marker MB or the marking pen 30 of the probe adapter 20 is arranged at the front surface of the ultrasonic probe 1 in the second and third embodiments, a marker MC is arranged at a side surface of the ultrasonic probe 1 in the fourth embodiment. Hereinafter, only the difference between the second and fourth embodiments will be described, and duplicate description is omitted.

Figure 8B:
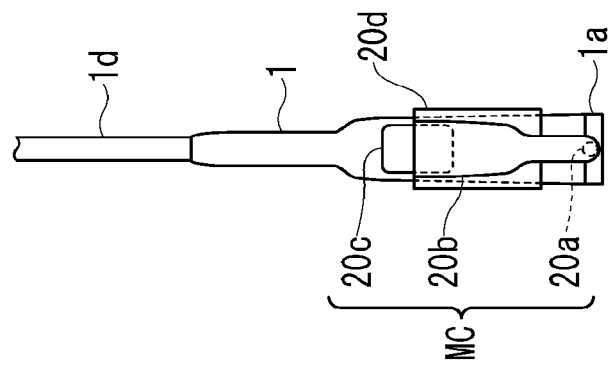
FIG. 8A, FIG. 8B, and FIG. 8C are plan views illustrating the probe adapter of the fourth embodiment.
Figure 8A:
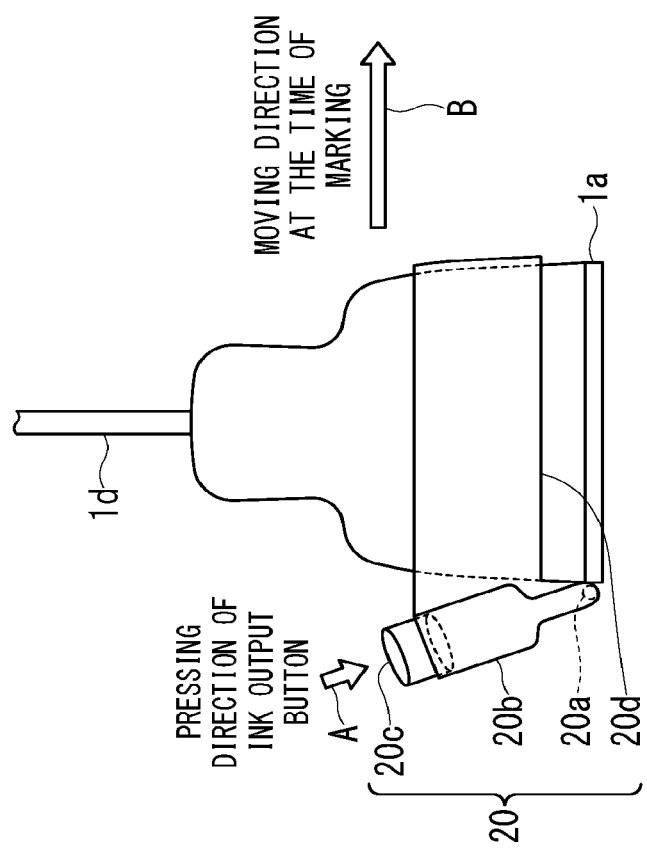
Figure 8C:

FIG. 8A, FIG. 8B, and FIG. 8C are plan views illustrating the probe adapter 20 of the fourth embodiment. FIG. 8A is a front view of the ultrasonic probe 1 to which the probe adapter 20 is attached, FIG. 8B is a side view of the ultrasonic probe 1 to which the probe adapter 20 is attached, and FIG. 8C is a bottom view of the ultrasonic probe 1 to which the probe adapter 20 is attached.

As shown in FIG. 8A, FIG. 8B, and FIG. 8C, in the fourth embodiment, the probe adapter 20 is attached to the ultrasonic probe 1 in such a manner that the marker MC is disposed on the left side surface of the ultrasonic probe 1. The probe adapter 20 includes the ink ejection port 20a, the ink tank 20b, the button 20c, and the holder 20d.

The arrow B in FIG. 8A indicates the moving direction of the ultrasonic probe 1 at the time of marking. A user such as a doctor apply ink to a skin surface of an object by pressing down the button 20c at the position where the user hopes to mark, while sliding the ultrasonic probe 1 in the direction of the arrow B.

Figure 9:
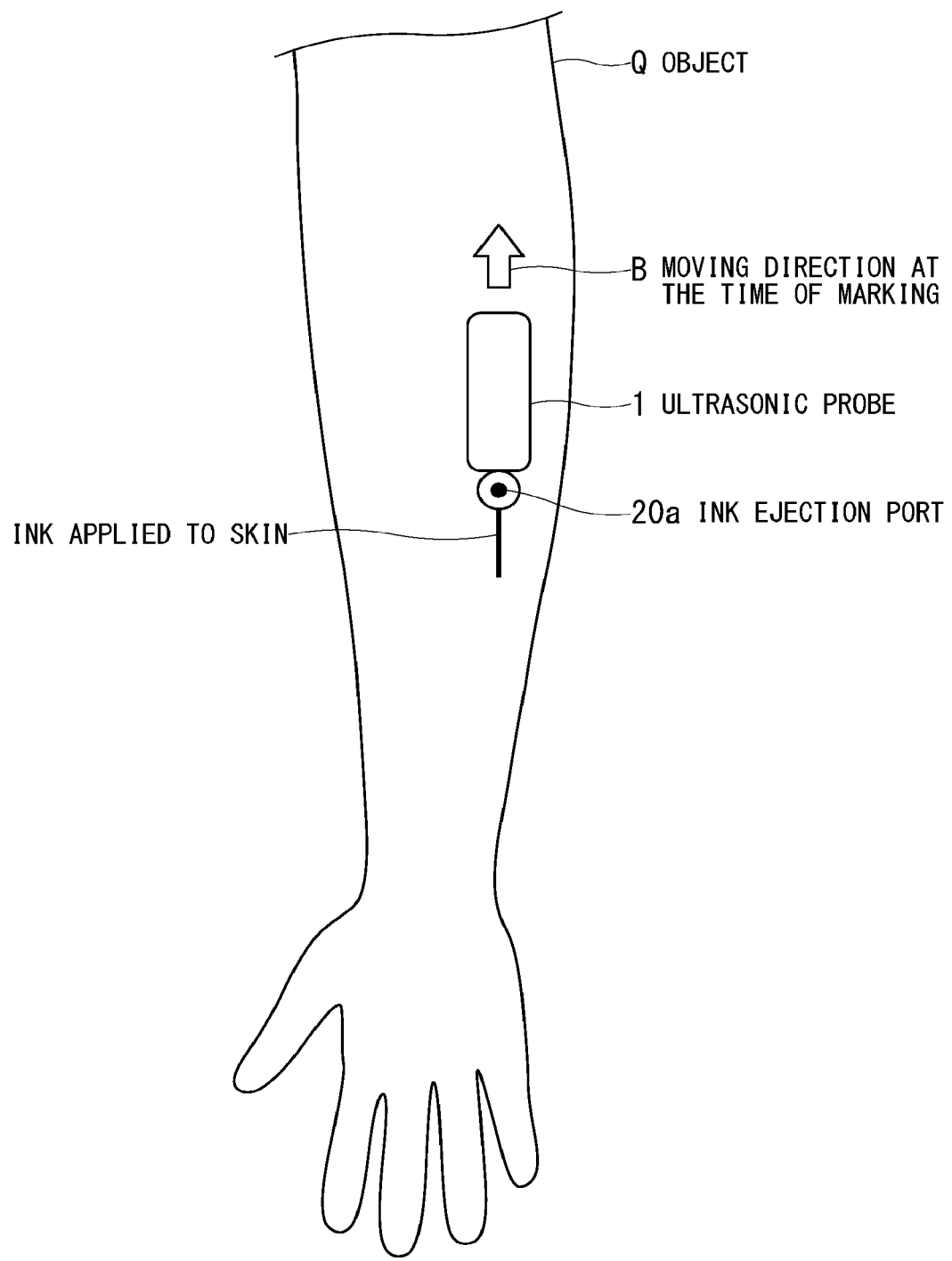
FIG. 9 is a schematic diagram illustrating a case of using the ultrasonic probe of the fourth embodiment.

FIG. 9 is a schematic diagram illustrating a case of using the ultrasonic probe 1 of the fourth embodiment. FIG. 9 illustrates a case where the ultrasonic probe 1 is moved on the skin surface of the arm of the object Q in the direction of the arrow B in a manner similar to FIG. 4. When the ultrasonic probe 1 is moved in the direction of the arrow B in FIG. 9, i.e., toward the upper arm side of the object Q while the button 20c of the ultrasonic probe 1 is being pressed, a trace of movement of the ultrasonic probe 1 is marked in a manner similar to the first embodiment.

FIG. 9 differs from the case of FIG. 4 in that FIG. 9 illustrates a case where a blood vessel of the arm is observed in the long-axis direction. In observation of a blood vessel along the long-axis direction, it is possible to observe how a stenosis region in this blood vessel is spread. In observation of a blood vessel along the long-axis direction, it is possible to identify the start part and the end part of the stenosis region, and, for instance, the range of the stenosis region can be indicated on the skin surface by marking at the start part and the end part of the stenosis region.

Although a description has been given of the case where ink is used for a marking means of the marker MC in the fourth embodiment, the marking means is not limited to ink. The marking pen 30 or adhesive material may be used for the marking means in the fourth embodiment instead of ink, and this point holds true for the fifth to eleventh embodiments.

As described above, the same effects as the first embodiment can also be obtained in the fourth embodiment. Further, the marker MC of the probe adapter 20 is disposed on the side surface of the ultrasonic probe 1 in the fourth embodiment. Thus, the fourth embodiment is advantageous in a case where marking is performed during movement of the ultrasonic probe 1 in the array direction like observation of a blood vessel in the long-axis direction.

Fifth Embodiment

Although a case of using one marker MC has been described in the fourth embodiment, number of the marker may be two or more. In the ultrasonic diagnostic apparatus 100 of the fifth embodiment, the probe adapter 20 includes two markers MD. Hereinafter, only the difference between the second and fifth embodiments will be described, and duplicate description is omitted.

FIG. 10A, FIG. 10B, and FIG. 10C are plan views illustrating the probe adapter 20 of the fifth embodiment. FIG. 10A is a front view of the ultrasonic probe 1 to which the probe adapter 20 is attached, FIG. 10B is a side view of the ultrasonic probe 1 to which the probe adapter 20 is attached, and FIG. 10C is a bottom view of the ultrasonic probe 1 to which the probe adapter 20 is attached.

As shown in FIG. 10, two markers MD are respectively provided on both side surfaces of the probe adapter 20 of the fifth embodiment. Each of the markers MD includes the ink ejection port 20a, the ink tank 20b, and the button 20c.

Thus, under the state where the probe adapter 20 is attached to the ultrasonic probe 1, the markers MD are disposed on both side surfaces of the ultrasonic probe 1. Under the state where the probe adapter 20 is attached, since the button 20c is disposed so as to be encircled the ultrasonic probe 1 as shown in FIG. 10B and FIG. 10C, it is possible to simultaneously output ink from both ink tanks 20b provided on both side surfaces of the probe adapter 20. Both buttons 20c uniformly applies pressure to respective ink tanks 20b of both side surfaces of the probe adapter 20 at the same time, and thus ink is simultaneously applied from the respective ink ejection ports 20a of both side surfaces.

Figure 11:
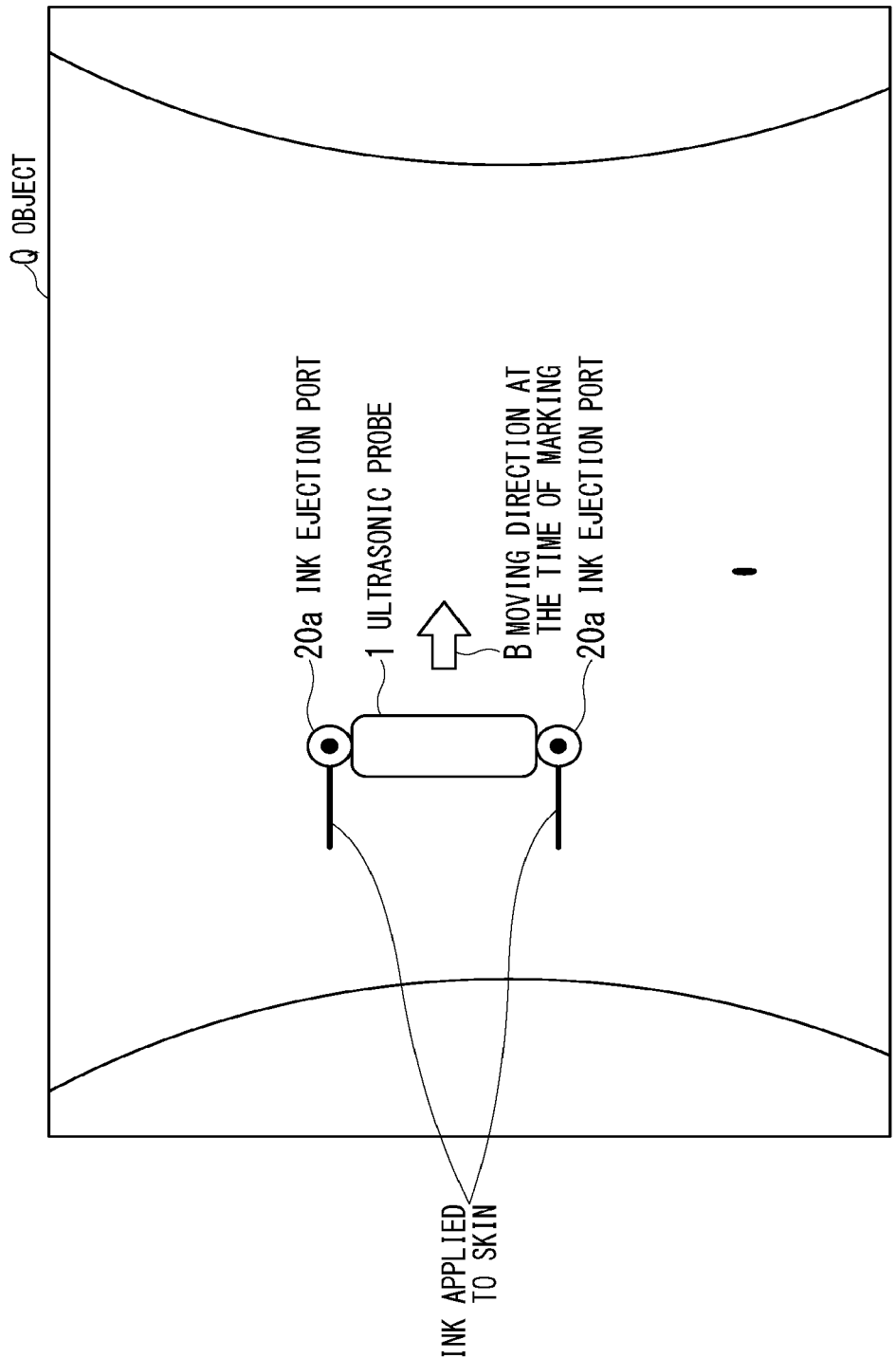
FIG. 11 a schematic diagram illustrating a case of using the ultrasonic probe of the fifth embodiment.

FIG. 11 a schematic diagram illustrating a case of using the ultrasonic probe 1 of the fifth embodiment. FIG. 11 illustrate a case where the ultrasonic probe 1 is moved on the skin surface of the abdomen of the object Q in the direction of the arrow B, i.e., in the horizontal direction of the sheet of FIG. 11. When a user moves the ultrasonic probe 1 on the skin surface of the abdomen of the object Q in the direction of the arrow B, i.e., in the horizontal direction of the sheet of FIG. 11 while pressing the button 20c of the ultrasonic probe 1, ink is applied to the skin surface of the object Q in accordance with movement of the ultrasonic probe 1. In this case, two lines are marked on the skin surface of the abdomen of the object Q, and those two lines indicate moving traces of both side surfaces of the ultrasonic probe 1.

As described above, the same effects as the first embodiment can also be obtained in the fifth embodiment. Further, two marking lines can be marked by one hand in the fifth embodiment. Moreover, by indicating the respective moving traces of both side surfaces of the ultrasonic probe 1 by two marking lines, it is possible to more precisely reproduce imaging regions imaged by the ultrasonic diagnostic apparatus 100.

Sixth Embodiment

The sixth embodiment is a case where the probe adapter 20 is provided with configuration of removing an ultrasonic medium such as ultrasonic jelly in addition to a marker. Hereinafter, only the difference between the second and sixth embodiments will be described, and duplicate description is omitted.

FIG. 12A, FIG. 12B, and FIG. 12C are plan views illustrating the probe adapter 20 of the sixth embodiment. FIG. 12A is a front view of the ultrasonic probe 1 to which the probe adapter 20 is attached, FIG. 12B is a side view of the ultrasonic probe 1 to which the probe adapter 20 is attached, and FIG. 12C is a bottom view of the ultrasonic probe 1 to which the probe adapter 20 is attached.

As shown in FIG. 12A, FIG. 12B, and FIG. 12C, the probe adapter 20 attached to the ultrasonic probe 1 is provided with a wiper 20e which removes an ultrasonic medium such as ultrasonic jelly. Prior to imaging an object with the use of the ultrasonic diagnostic apparatus 100, an ultrasonic medium such as ultrasonic jelly is coated on a skin surface of an object. Ultrasonic jelly is water-soluble lubricant, and approximately 90% of ultrasonic jelly is water in terms of composition. By coating such ultrasonic jelly on a skin surface of an object, it is possible to avoid that air is included between the ultrasonic probe 1 and the skin surface of the object, and thus transmission efficiency of ultrasonic waves from the ultrasonic probe 1 is enhanced. Additionally, by coating ultrasonic jelly on a skin surface of an object, smoothness on a skin surface of an object is enhanced with respect to the ultrasonic probe 1, and operability of the ultrasonic probe 1 is enhanced.

However, when marking is performed with a marking means such as ink on a skin surface of an object on which ultrasonic jelly is coated, ink does not adhere to the skin surface of the object due to existence of ultrasonic jelly in some cases. Additionally, in some cases, ink bleeds due to existence of water-soluble ultrasonic jelly and marking cannot be precisely performed.

For those reasons, the wiper 20e is disposed at the position closest to the marker ME on the internal wall of the probe adapter 20 so that the wiper 20e can efficiently remove an ultrasonic medium such as ultrasonic jelly. Accordingly, an ultrasonic medium is used at the time of imaging, and this ultrasonic medium is removed at the time of marking such that ink easily adhere to a skin surface of an object.

The arrow B in FIG. 12B indicates the moving direction of the ultrasonic probe 1 at the time of marking. A user such as a doctor apply ink to a skin surface of an object while sliding the ultrasonic probe 1 in the direction of the arrow B. In this case, the probe head 1a passes on the skin surface of the object under the state where ultrasonic jelly is coated on the skin surface. When the probe head 1a passes on the skin surface of the object, the ultrasonic jelly is removed from the skin surface by the wiper 20e and ink is applied by the marker ME immediately after the removal of the ultrasonic jelly. As described above, marking can be efficiently performed by removing the ultrasonic jelly from a skin surface of an object by the wiper 20e.

Note that a wiper head 20f is provided on the surface of the wiper 20e to be brought into contact with a skin surface of an object as shown in FIG. 12A, FIG. 12B, and FIG. 12, and this wiper head 20f is composed of, e.g., soft or elastic material such as silicone and/or rubber so as to protect a skin of an object. Additionally, since the wiper head 20f is closely-attached to a skin of an object, it is possible to efficiently remove an ultrasonic medium coated on the skin surface of the object.

Further, as shown in FIG. 12B, the wiper 20e is formed so as to have predetermined width from between the marker ME and the probe head 1a along both side surfaces of the marker ME. The bottom view of FIG. 12C indicates the V-shaped wiper 20e being bent at the position of ink ejection port 20a, when viewed from the side of the probe head 1a. However, the shape of the wiper 20e is not limited to the shape shown in FIG. 12A to FIG. 12C.

Figure 13:
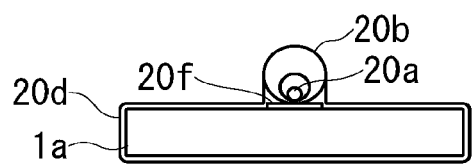
FIG. 13 is a bottom view illustrating a probe adapter which includes a modification of the wiper of the sixth embodiment.

FIG. 13 is a bottom view illustrating the probe adapter 20 which includes a modification of the wiper 20e of the sixth embodiment.

The modification shown in FIG. 13 differs from the wiper 20e shown in FIG. 12C in that the wiper 20e is provided between the marker ME and the probe head 1a so as to be in parallel with the array direction of the transducers inside the ultrasonic probe 1. When the long-axis direction of the wiper 20e is defined as the direction in parallel with the array direction, it is desirable that length of the wiper 20e in the long-axis direction is equal to or longer than the size of the ink ejection port 20a of the marker. When this condition is satisfied, it is possible to more steadily (reliably) remove an ultrasonic medium coated on a skin surface of an object.

As described above, the same effects as the first embodiment can also be obtained in the sixth embodiment. Further, the probe adapter 20 of the ultrasonic diagnostic apparatus 100 of the sixth embodiment is equipped with the wiper 20e which removes an ultrasonic medium coated on a skin surface of an object. According to such configuration, it is possible to avoid that ink applied from the marker is repelled or bleeds due to a water-soluble ultrasonic medium resulting in failure of marking a skin surface of an object. According to the sixth embodiment as described above, it is possible to precisely mark a skin surface of an object by applying ink to the skin surface after removing an ultrasonic medium from a skin surface.

Seventh Embodiment

The seventh embodiment is a case where the probe adapter 20 further includes an angle adjuster 20g configured to adjust an angle between the ultrasonic probe 1 and the wiper 20e in addition to the respective components of the probe adapter 20 of the sixth embodiment. Hereinafter, only the difference between the second and seventh embodiments will be described, and duplicate description is omitted.

A user such as a doctor sometimes tilts the ultrasonic probe 1 by a predetermined angle with respect to a skin surface of an object when operating the ultrasonic probe 1 so as to acquire ultrasonic images. Since a transmission angle of an ultrasonic wave can be easily changed by tilting the ultrasonic probe 1, it is possible to depict a structure at a different position or in different depth inside an object by tilting the ultrasonic probe 1.

When the wiper 20e is separated from a skin surface of an object due to change in angle of the ultrasonic probe 1, it is difficult to efficiently remove an ultrasonic medium. For this reason, the probe adapter 20 of the seventh embodiment includes the angle adjuster 20g configured to adjust an angle between the ultrasonic probe 1 and the wiper 20e. Thus, the probe adapter 20 of the seventh embodiment can maintain the state in which the wiper 20e is in contact with a skin surface of an object, even when the ultrasonic probe 1 is tilted.

Figure 14:
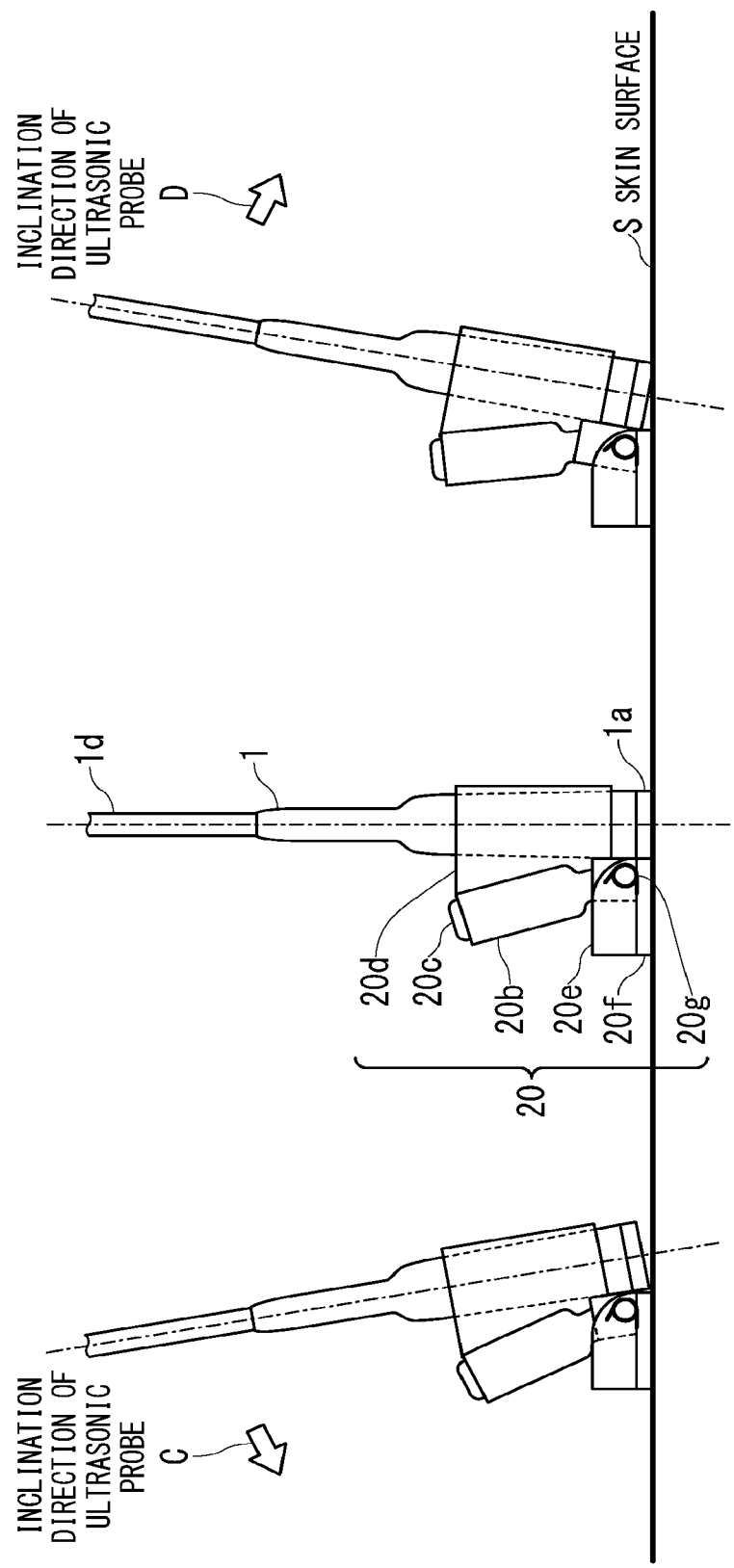
FIG. 14 is a plan view illustrating the probe adapter of the seventh embodiment.

FIG. 14 is a plan view illustrating the probe adapter 20 to be attached to the ultrasonic probe 1 in the seventh embodiment. The left part of FIG. 14 is a side view when the ultrasonic probe 1 is tilted in the direction of the arrow C, and the right part of FIG. 14 is a side view when the ultrasonic probe 1 is tilted in the direction of the arrow D. The central part of FIG. 14 illustrates the state where the central axis of the ultrasonic probe 1 indicated by a chain line is approximately perpendicular to the skin surface S of the object.

The marker of the probe adapter 20 shown in FIG. 14 includes the ink tank 20b, the button 20c, and a non-illustrated ink ejection port. The probe adapter 20 shown in FIG. 14 is equipped with the angle adjuster 20g at the connection part between the marker and the wiper 20e and this angle adjuster 20g is configured of, e.g., an elastic body such as a spring. The angle adjuster 20g adjusts the angle between the ultrasonic probe 1 and the skin surface S so as to cause the wiper head 20f to be kept in contact with the skin surface S of the object, even when the angle between the ultrasonic probe 1 and the skin surface S is changed as shown in FIG. 14.

In the case of FIG. 14, there is a region where the probe head 1a is not closely-attached to the skin surface S, when the ultrasonic probe 1 is tilted in the inclination direction C or in the inclination direction D. In a region where the probe head 1a is not closely-attached to the skin surface S, there is an ultrasonic medium such as jelly. Thus, even when the probe head 1a is not closely-attached to the skin surface S, it is possible to acquire ultrasonic images with satisfactory image quality.

However, unless the wiper head 20f is closely-attached to the skin surface S, it is difficult to efficiently remove an ultrasonic medium such as jelly from the skin surface S. Thus, as shown in FIG. 14, the angle adjuster 20g adjusts the above-described angle so as to cause the wiper head 20f to be kept in contact with the skin surface S regardless of the inclination of the ultrasonic probe 1.

As described above, the same effects as the first embodiment can also be obtained in the seventh embodiment. Further, in the ultrasonic diagnostic apparatus 100 of the seventh embodiment, the wiper 20e is continuously kept in contact with the skin surface S of the object during imaging regardless of the inclination of the ultrasonic probe 1. Since an ultrasonic medium can be efficiently removed by the wiper 20e even when the ultrasonic probe 1 is moved in the state of being tiled, marking can be performed on the skin surface S of the object regardless of the inclination angle of the ultrasonic probe 1 during its movement on the skin surface S.

Eighth Embodiment

In the eighth embodiment, the wiper 20e is brought into contact with a skin surface of an object in each period during which marking is performed, and is separated from the skin surface of the object in all the other periods during which marking is not performed.

For this reason, the probe adapter 20 of the eighth embodiment includes a slide mechanism configured to slide and move the wiper 20e. When it is not necessary to remove an ultrasonic medium, the slide mechanism separates the wiper 20e from the skin surface S of the object. Conversely, when it is required to remove an ultrasonic medium, the slide mechanism brings the wiper 20e into contact with the skin surface S of the object. Hereinafter, only the difference between the sixth and eighth embodiments will be described, and duplicate description is omitted.

Figure 15:
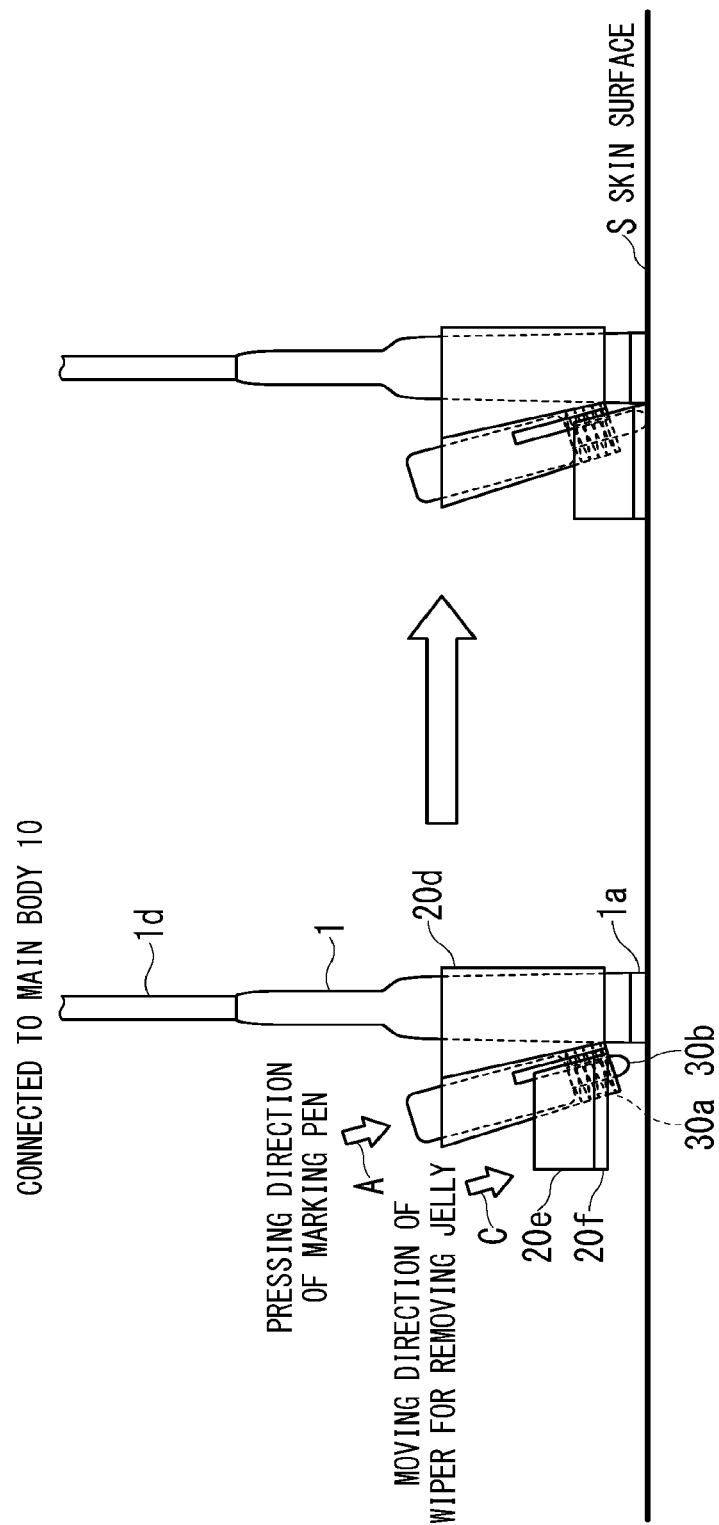
FIG. 15 is a plan view illustrating the probe adapter of the eighth embodiment.

FIG. 15 is a plan view illustrating the probe adapter 20 of the eighth embodiment. FIG. 15 illustrates two side views of the ultrasonic probe 1. The right side of FIG. 15 illustrates the position of the wiper 20e when marking is performed, and the left side of FIG. 15 illustrates the position of the wiper 20e when marking is not performed.

The case shown in FIG. 15 differs from the sixth embodiment in that the marker is configured as a marking pen 30. As described in the third embodiment, the marking pen 30 includes the adjuster 30a configured of an elastic body such as a spring. Thus, when marking is performed on the skin surface S of the object, the tip 30b of the marking pen 30 is adjusted by the adjuster 30a so as to be in contact with the skin surface S of the object. Conversely, when marking is not performed, the tip 30b of the marking pen 30 is adjusted by the adjuster 30a so as to be at a position separated from the skin surface S of the object.

The left side of FIG. 15 illustrates a case where the wiper 20e slides in the direction of the arrow C in conjunction with an operation of pressing down the marking pen 30 in the pressing direction of the arrow A. The right side of FIG. 15 is a side view of the probe adapter 20 illustrating the state where the marking pen 30 is pressed down, and indicates the pressing direction of the marking pen 30 along the central axis of the marking pen 30.

The wiper 20e may be provided with, e.g., a protrusion structure configured to slide the wiper 20e toward the skin surface S of the object along a groove, which is formed on the cylindrical structure and is capable of housing the marking pen 30. Additionally, a stopper may be provided on the groove formed on the cylindrical structure of housing the marking pen 30 such that this stopper can hook and fix the marking pen 30 at a position where the wiper 20e is in contact with the skin surface S or is separated from the skin surface S. Note that the wiper 20e may be configured to slide as a component independent of the marking pen 30.

When ink and/or an adhesive material is used for a marking means instead of the marking pen 30, since ink is applied to the skin surface S of the object when the button is pressed down, the wiper 20e may be configured to slide in conjunction with an operation of pressing the button.

Although a description has been given of the case where the wiper 20e is manually slid, the adapter 20 may be configured such that the wiper 20e is electrically slid.

As described above, the same effects as the first embodiment can also be obtained in the eighth embodiment. Further, the ultrasonic diagnostic apparatus 100 of the eighth embodiment can bring the wiper 20e into contact with the skin surface S of the object, only when the wiper 20e is used. Thus, marking can be performed on the skin surface S of the object, while an ultrasonic medium is being removed by the wiper 20e as needed.

Ninth Embodiment

In the first to eighth embodiments, descriptions have been given of the cases where marking is performed on a skin surface of an object by the ultrasonic probe 1 equipped with the marker or the ultrasonic probe 1 to which the probe adapter 20 equipped with the marker is attached. Hereinafter, the ultrasonic diagnostic apparatus 100 operates in cooperation with the ultrasonic probe 1 equipped with the marker or the ultrasonic probe 1 to which the probe adapter 20 equipped with the marker is attached, when marking is performed on a skin surface of an object.

The ninth embodiment relates to the ultrasonic diagnostic apparatus 1 equipped with an ultrasonic probe to which the probe adapter 20 equipped with an ink head as a marking means is attached. Hereinafter, only the difference between the second and ninth embodiments will be described, and duplicate description is omitted.

Figure 16:
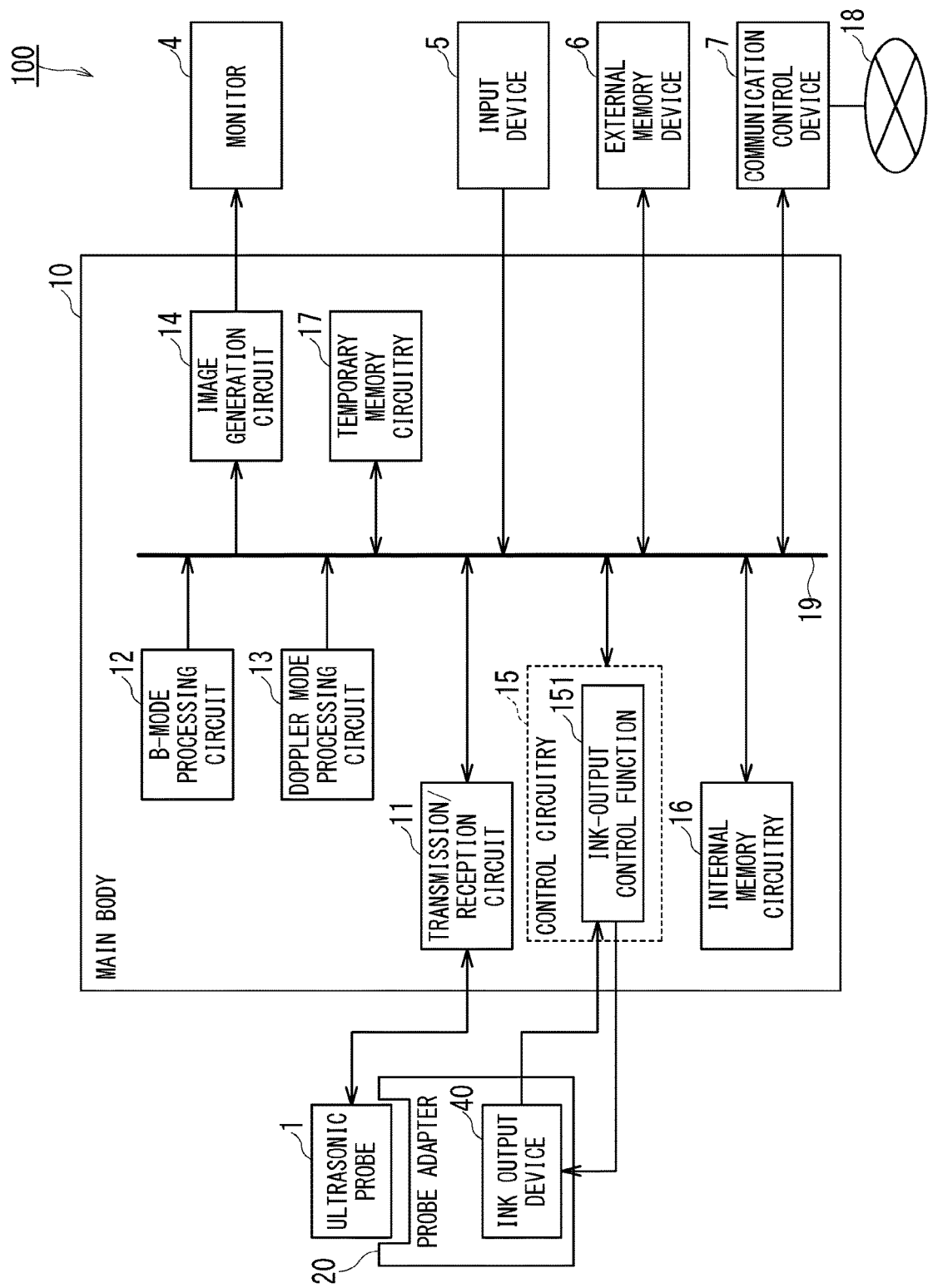
FIG. 16 is a general block diagram illustrating configuration of the ultrasonic diagnostic apparatus of the ninth embodiment.

FIG. 16 is a general block diagram illustrating configuration of the ultrasonic diagnostic apparatus 100 of the ninth embodiment. As shown in FIG. 16, the ultrasonic diagnostic apparatus 100 of the ninth embodiment includes an ink output device 40 and an ink-output control function 151 in addition to all the components of the second embodiment.

The ink output device 40 is disposed in the holder 20d of the probe adapter 20, and includes, e.g., an ink tank, an ink head, and a button. The ink output device 40 further includes a power supply cable for supplying electric power to the ink head, and is connected to the main body 10 via this power supply cable. Configuration of the probe adapter 20 equipped with the ink output device 40 will be described below in detail by referring to FIG. 17. Note that the ink output device 40 maybe integrally provided on the ultrasonic probe 1 like the first embodiment.

The control circuitry 15 further includes the ink-output control function 151. The ink-output control function 151 receives an ink-output request signal from the ink output device 40 and transmits an ink-output enabling signal to the ink output device 40. The ink-output request signal is, e.g., transmitted to the ink-output control function 151 via the power supply cable when a button of the ink output device 40 is pressed. Similarly, the ink-output enabling signal from the ink-output control function 151 is transmitted to the ink output device 40 via the power supply cable.

More specifically, according to the ink-output control function 151 determines whether the following first and second conditions are satisfied or not, and transmits the ink-output enabling signal to the ink output device 40 when both of the first and second conditions are satisfied. The first condition is that the ink-output control function 151 is immediately after receiving the ink-output request signal. The second condition is that ink remaining amount in the ink output device 40 is sufficient. When at least one of the first and second conditions is not satisfied, the ink-output control function 151 causes the main body 10 to output a beep sound and causes the monitor 4 to display the content of the condition which is not satisfied. In this manner, a user can be informed of the reason why ink cannot be outputted.

Figure 17A:
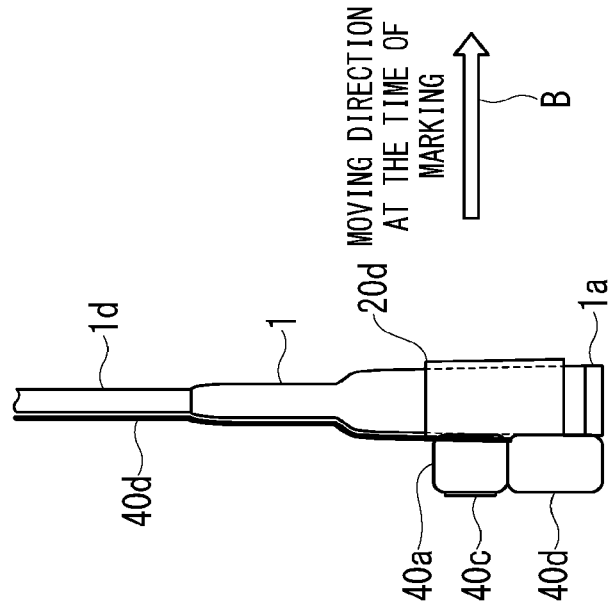
FIG. 17A, FIG. 17B, and FIG. 17C are plan views illustrating the probe adapter of the ninth embodiment.
Figure 17B:
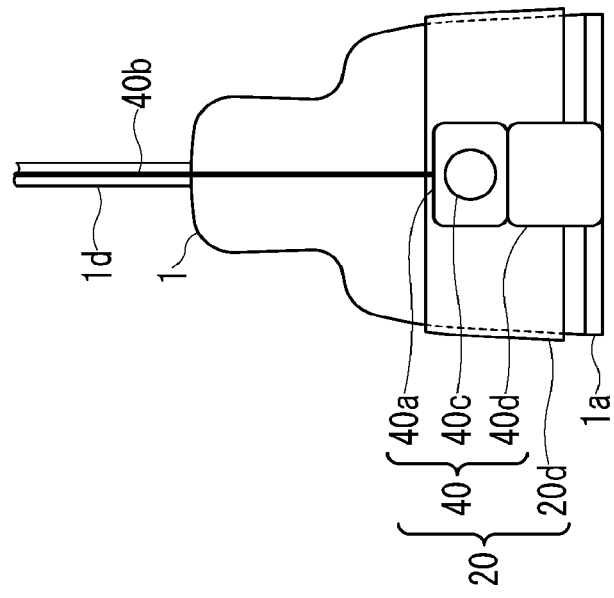
Figure 17C:
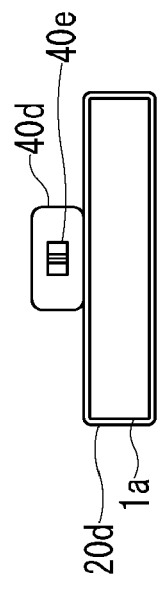

FIG. 17A, FIG. 17B, and FIG. 17C are plan views illustrating the probe adapter 20 of the ninth embodiment. FIG. 17A is a front view of the ultrasonic probe 1 to which the probe adapter 20 is attached, FIG. 17B is a side view of the ultrasonic probe 1 to which the probe adapter 20 is attached, and FIG. 17C is a bottom view of the ultrasonic probe 1 to which the probe adapter 20 is attached.

As shown in FIG. 17A, FIG. 17B, and FIG. 17C, the ink output device 40 includes the ink tank 40a, the ink head 40d, and the button 40c, and is connected to the main body 10 via the power supply cable 40b for acquiring electric power necessary for operating the ink head 40d from the main body 10.

The ink head 40d includes an ink-head nozzle 40e as shown in FIG. 17C. Ink inside the ink tank 40a is ejected from the ink-head nozzle 40e, and thereby ink is applied to a skin surface of an object.

A fine tube formed from piezoelectric material is provided inside the ink head 40d, the inside of this fine tube is filled with ink inside the ink tank 40a by capillary action. This fine tube of the ink head 40d is connected to the ink-head nozzle 40e. When the ink head 40d receives the ink-output enabling signal from ink-output control function 151, voltage is applied to this fine tube, and thus inner pressure of this fine tube is raised and ink is ejected from the ink-head nozzle 40e.

Although a description has been given of the case where the ink tank 40a is disposed at the upper part of the ink head 40d as a component independent of the ink head 40d in FIG. 17A, FIG. 17B, and FIG. 17C, the ink tank 40a and the ink head 40d may be integrally configured.

Next, a description will be given of a case where the ink output device 40 operates in cooperation with the ultrasonic diagnostic apparatus 100.

Figure 18:
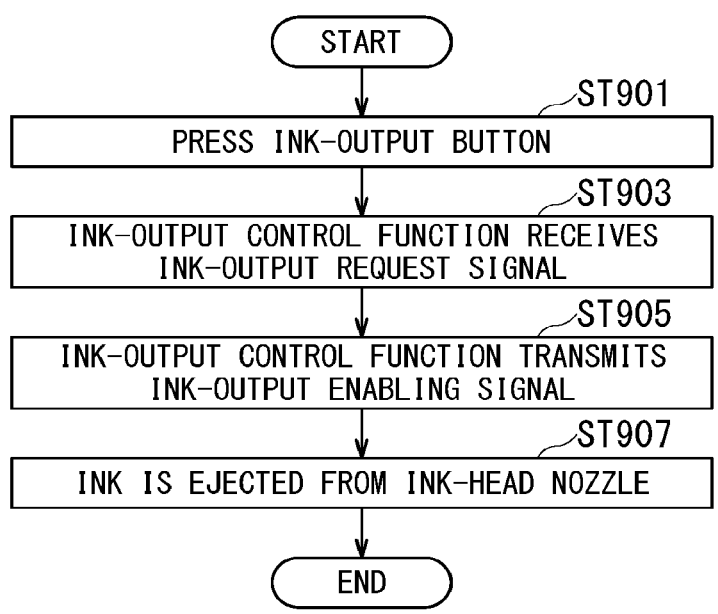
FIG. 18 is a flowchart illustrating an operation performed by the ultrasonic diagnostic apparatus of the ninth embodiment.

FIG. 18 is a flowchart illustrating an operation performed by the ultrasonic diagnostic apparatus 100 of the ninth embodiment.

In the step ST901, a user presses down the button 40c of the ink output device 40. When the button 40c is pressed down, the ink-output request signal is transmitted from the ink output device 40 to the main body 10 via the power supply cable 40b.

In the step ST903, the ink-output control function 151 of the main body 10 receives the ink-output request signal from the ink output device 40.

In the step ST905, the ink-output control function 151 transmits the ink-output enabling signal to the ink output device 40 via the power supply cable 40b.

In the step ST907, the ink head 40d ejects ink from the ink-head nozzle 40e in response to the ink-output enabling signal, and applies ink to a skin surface of an object.

Although a description has been given of the case where ink is ejected from the ink head 40d each time the button 40c is pressed down in the flowchart of FIG. 18, an operation of the ink-output control function 151 is not limited to the case of FIG. 18. For instance, the ink-output control function 151 may be configured to be capable of distinguishing between an ink output state and an ink stop state. Specifically, the ink-output control function 151 transmits the ink-output enabling signal to the ink output device 40 via the power supply cable 40b when receiving the ink-output request signal under the ink stop state, and transmits the ink-output stop signal to the ink output device 40 via the power supply cable 40b when receiving the ink-output request signal under the ink output state.

Note that the ink-output request signal may be directly transmitted to the ink head 40d, and the ink head 40d may be configured so as to operate by receiving power supply for ink output via the power supply cable 40b.

Additionally, a wiper for removing an ultrasonic medium may be provided between the ink-head nozzle 40e and the probe head 1a as described in the sixth embodiment.

Further, the ink head 40d may be slidably mounted on the adapter 20 in such a manner that the ink-head nozzle 40e can move on a plane which is in parallel with a skin surface of an object. The ink head 40d may be configured to be manually slid or to be electrically slid. For instance, the ink head 40d may be further provided with a scanning mechanism which moves in the direction to the array direction and the elevation direction while causing the ink-head nozzle 40e to eject ink. When the ink head 40d is provided with such a scanning mechanism, the ink head 40d can freely change line width to be drawn on a skin surface of an object and can draw a figure and/or a letter by marking.

Moreover, the ink tank 40a may be provided with plural types of ink corresponding to respective chromatic colors. Control signals related to shape and color of marking are transmitted to the ink head 40d via the power supply cable 40b.

As described above, the same effects as the first embodiment can also be obtained in the ninth embodiment. Further, in the case of the ultrasonic diagnostic apparatus 100 of the ninth embodiment, a user can mark on a skin surface of an object only by a simple operation of lightly pressing down the button 40c with one hand. Moreover, in the case of changing a type of marking and/or colors of marking, for instance, a user can easily change it by inputting a desired type and/or color to the ultrasonic diagnostic apparatus 100 via the input device 5.

Tenth Embodiment

The tenth embodiment relates to the ultrasonic diagnostic apparatus 100 configured to determine an ink-output position of the probe adapter 20 by a magnetic sensor and to superimpose an ink applying position on an ultrasonic image being displayed. Hereinafter, only the difference between the ninth and tenth embodiments will be described, and duplicate description is omitted.

As an example here, the ink-output position means a position where a marking output means such as an ink ejection port and an ink head is located in terms of position at which a marking means such as ink on a skin surface of an object. Further, the ink applying position means both of (a) an actual ink applying position on a skin surface of an object where ink is actually applied and (b) a virtual ink applying position on a skin surface of an object where ink is estimated to be applied when ink is outputted from the above-described ink-output position.

Figure 19:
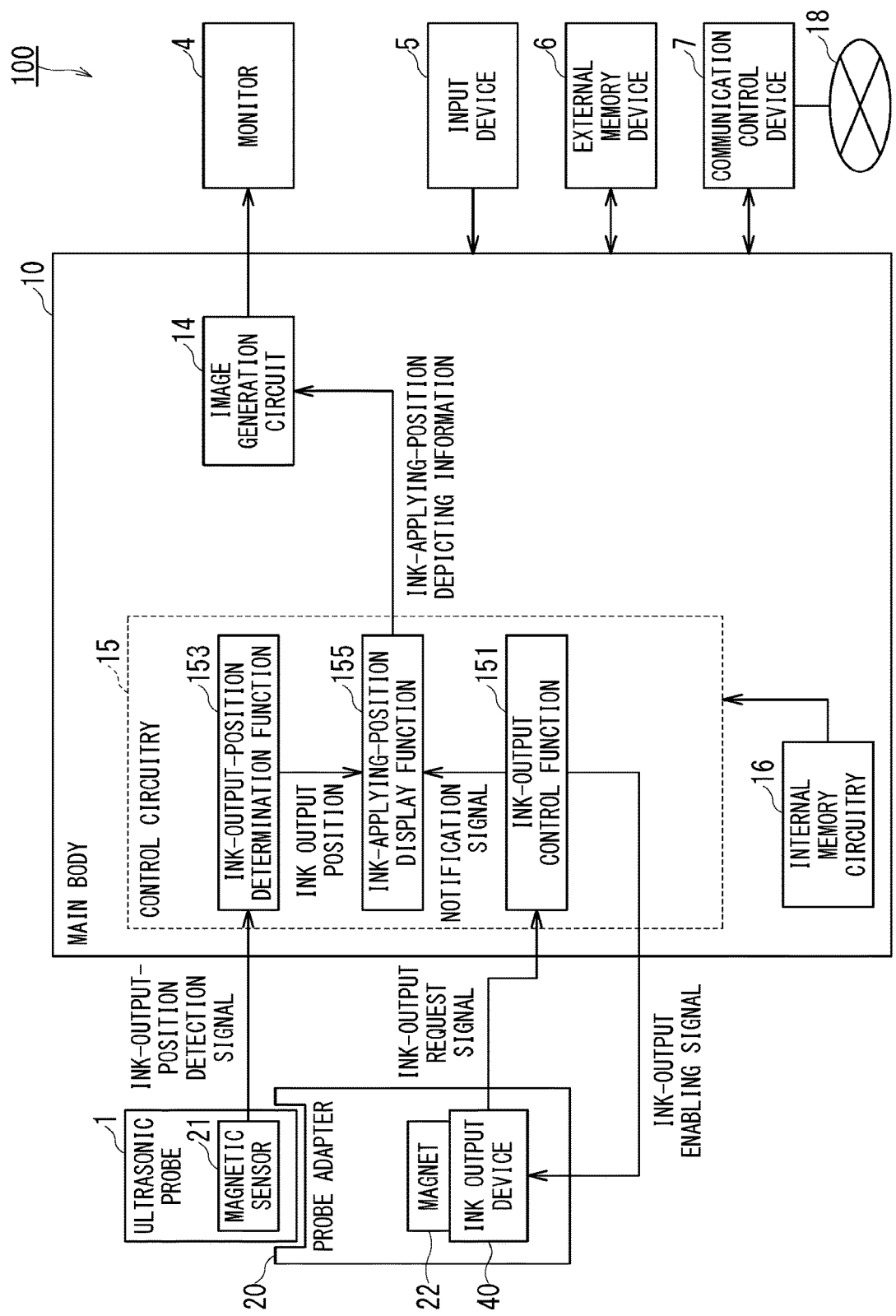
FIG. 19 is a general block diagram illustrating configuration of the ultrasonic diagnostic apparatus of the tenth embodiment.

FIG. 19 is a general block diagram illustrating configuration of the ultrasonic diagnostic apparatus 200 of the tenth embodiment. The tenth embodiment differs from the ninth embodiment (FIG. 16) in the following three points. Firstly, the ultrasonic probe 1 of the tenth embodiment further includes plural magnetic sensors 21. Secondly, the probe adapter 20 further includes a magnet 22. Thirdly, the control circuitry 15 of the main body 10 further includes an ink-output-position determination function 153 and an ink-applying-position display function 155.

Each of the magnetic sensors 21 is configured of, e.g., a hole element, and is disposed inside the housing of the ultrasonic probe 1. The plural magnetic sensors 21 are disposed at predetermined intervals, and detect magnetism generated by the magnet 22 disposed in the probe adapter 20. Each of the magnetic sensors 21 is a device configured to generate an induced current from magnetic flux change caused by the existence of the magnet 22 and to convert the detected magnetism into an electric signal. The magnetic sensors 21 transmit the ink-output-position detection signal to the ink-output-position determination function 153 of the main body 10.

The magnet 22 is disposed at the ink-output position of the marker provided on the probe adapter 20. The probe adapter 20 may be configured such that the magnet 22 moves in conjunction with movement of the ink-output position. Configuration of the magnet 22 and the magnetic sensors 21 will be described below in detail by referring to FIG. 20. Additionally, a method of determining the ink-output position of the probe adapter 20 is not limited to the above-describes aspect. For instance, the probe adapter 20 may be configured so as to detect a position of the marker with an infrared-ray sensor.

The ink-output-position determination function 153 determines the ink-output position of the probe adapter 20 on the basis of the ink-output-position detection signal detected by the magnetic sensors 21. Additionally, the ink-output-position determination function 153 may determine whether the probe adapter 20 is attached to the ultrasonic probe 1 or not, on the basis of the ink-output-position detection signal detected by the magnetic sensors 21.

The ink-output position for each type of the probe adapter 20 may be stored in the internal memory circuitry 16. Additionally, the ink-output position may be determined on the basis of the position of one magnetic sensor 21 which has detected the magnet 22, when plural magnetic sensor 21 are provided.

The ink-applying-position display function 155 superimposes and displays an ink applying position with respect to a skin surface of an object on an ultrasonic image by a line and/or a figure. The method of displaying an ink applying position on an ultrasonic image will be described below in detail by referring to FIG. 22 and FIG. 23.

First, a description will be given of the configuration of the ultrasonic probe 1 equipped with the magnetic sensors 21 and the configuration of the probe adapter 20 equipped with the magnet 22.

Figure 20:
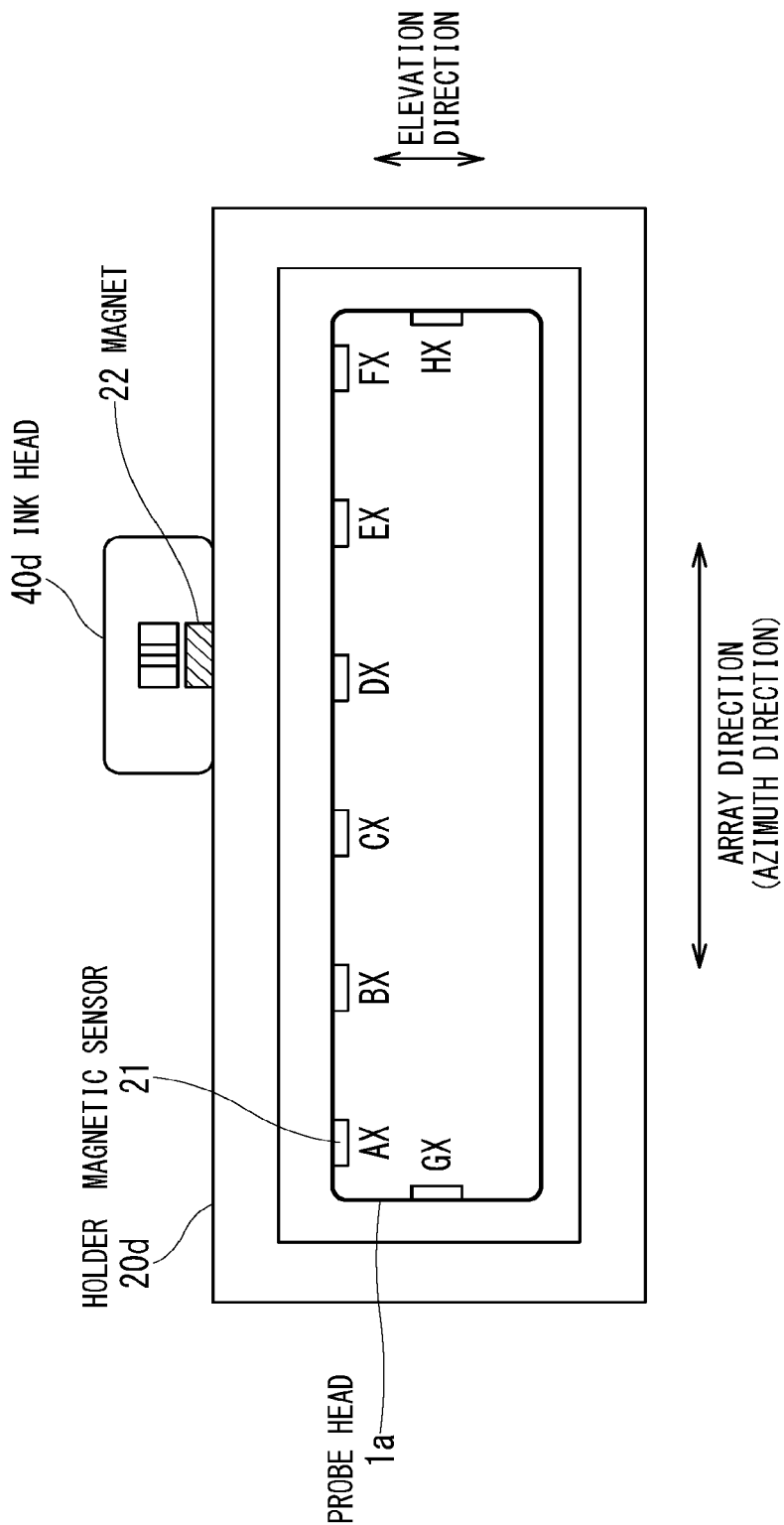
FIG. 20 is a schematic cross-sectional view of the bottom part of the ultrasonic probe in the state of being connected to the probe adapter of the tenth embodiment.

FIG. 20 is a schematic cross-sectional view of the bottom part of the ultrasonic probe 1 in the state of being connected to the probe adapter 20 of the tenth embodiment, and the cross-section of the probe adapter 20 is also illustrated outside the ultrasonic probe 1. FIG. 20 illustrates a case where the ink head 40d is used for a marking means. As shown in FIG. 20, plural magnetic sensors 21 are disposed inside the housing of the ultrasonic probe 1. In FIG. 20, the eight alphabetical signs AX to HX are given at the respective installment positions of a total of eight magnetic sensor 21 for distinguishing between the eight magnetic sensors 21.

In the case of FIG. 20, out of the eight magnetic sensors 21, six magnetic sensors 21 are provided at the front surface side of the ultrasonic probe 1, i.e., at the positions AX, BX, CX, DX, EX, and FX from the left of the sheet of FIG. 20 in order along the array direction. Additionally, the rest two magnetic sensors 21 are respectively installed at both side surfaces of the ultrasonic probe 1, i.e., at the position GX and the position HX along the elevation direction. Although a description has been given of the case where plural magnetic sensors 21 are provided in the array direction and plural magnetic sensors 21 are provided also in the elevation direction in FIG. 20, positions and number of the magnetic sensors 21 are not limited to the aspect of FIG. 20.

Each of the magnetic sensors 21 can generate voltage in accordance with magnetic flux density. In other words, each of the magnetic sensor 21 can compute distance from the magnet 22 on the basis of magnetic flux density. Thus, the ink-output-position determination function 153 maybe configured so as to identify the ink-output position of the ink head 40*d* by computing distance from the magnet 22 with the use of at least two magnetic sensors 21.

Inside the ink head 40*d* of the probe adapter 20 in FIG. 20, the magnet 22 is provided at the position of the ink-head nozzle 40*e* outputting ink on the side of the ultrasonic probe 1. In the case of FIG. 20, the magnet 22 inside the ink head 40*d* faces the magnetic sensor 21 at the position DX in the probe head 1*a*. In this case, the magnetic sensor 21 at the position DX (i.e., at the position closest to the magnet 22) detects magnetism generated by the magnet 22 installed on the ink head 40*d*, then converts the detected magnetism into voltage, and then transmits the voltage signal as the ink-output-position detection signal to the main body 10. The ink-output-position determination function 153 of the main body 10 determines the ink-output position of the ink head 40*d* on the basis of the ink-output-position detection signal from the magnetic sensor 21 at the position DX.

When the ink head 40*d* is located at the position at which the ink head 40*d* faces (or is closest to) the position AX, BX, CX, EX, FX, GX, or HX, the same operation as described above is performed. It is possible to detect the position of the ink-head nozzle 40*e* configured to output ink by arranging appropriate number of magnetic sensors 21 at intervals inside the housing of the ultrasonic probe 1.

Figure 21:
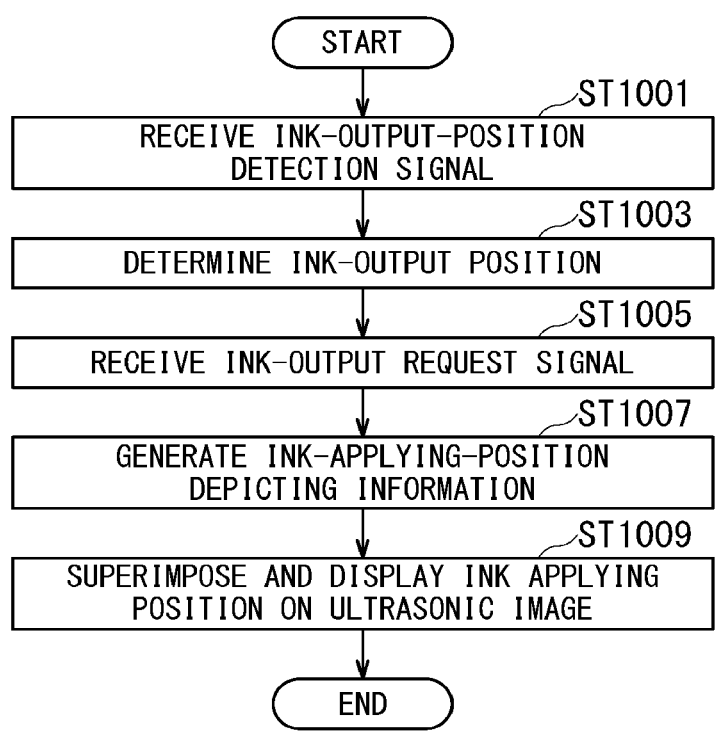
FIG. 21 is a flowchart illustrating an operation performed by the ultrasonic diagnostic apparatus of the tenth embodiment.

FIG. 21 is a flowchart illustrating an operation performed by the ultrasonic diagnostic apparatus 100 of the tenth embodiment.

In the step ST1001, the ink-output-position determination function 153 receives the ink-output-position detection signal detected by one of the magnetic sensors 21.

In the step ST1003, the ink-output-position determination function 153 determines the ink-output position. The ink-output position is determined on the basis of the respective positions of the magnetic sensors 21 installed in the ultrasonic probe 1. The respective positions of the magnetic sensors 21 are determined on the basis of the magnetic sensor 21 which has transmitted the ink-output-position detection signal to the main body 10. Additionally, on the basis of the ink-output-position detection signal from the magnetic sensor 21, the ink-output-position determination function 153 may detect that the probe adapter 20 is attached to the ultrasonic probe 1. The ink-output-position determination function 153 may determine the ink-output position from tabulated list data indicative of an ink-output position for each type of probe adapter stored in the internal memory circuitry 16, on the basis of the type of the probe adapter inputted by a user.

In the step ST1005, the ink-output control function 151 receives the ink-output request signal generated by pressing the button 40*c*. In response to this reception, a notification signal is transmitted from the ink-output control function 151 to the ink-applying-position display function 155. The notification signal is a signal of informing the ink-applying-position display function 155 that an ink output request is inputted from a user.

Additionally, when the ink-output control function 151 receives the ink-output request signal, the ink-output control function 151 transmits the ink-output enabling signal to the ink output device 40. In the tenth embodiment, the ink-output enabling signal is transmitted to the ink output device 40 in a manner similar to the ninth embodiment, when the first and second conditions are satisfied. The first condition is that the current time is immediately after receiving the ink-output request signal, and the second condition is that ink remaining amount inside the ink output device 40 is sufficient.

In the step ST1007, in response to the notification signal, the ink-applying-position display function 155 generates ink-applying-position depicting information on the basis of the ink-output position determined by its ink-output-position determination function 153. The ink-applying-position depicting information is, e.g., information on a figure and/or sign indicating an ink applying position and positional information on where such a figure and/or sign is displayed. It is possible to designate a display position of a figure and/or sign indicating an ink applying position by, e.g., pixel number from the left edge of the ultrasonic image and pixel number from the top edge of the ultrasonic image, under the assumption that the side of the skin surface of the object is the top side of the ultrasonic image.

In the step ST1009, the image generation circuit 14 superimposes and displays the ink applying position on an ultrasonic image on the basis of the ink-applying-position depicting information.

Note that the order of the processing from the steps ST1001 to ST1005 is not limited to the order in the flowchart of FIG. 21. Additionally, the ink-applying-position display function 155 may generate the ink-applying-position depicting information in the processing of the step ST1007 without receiving the ink-output enabling signal in the step ST1005 such that the ink applying position is superimposed and displayed on the ultrasonic image in the step ST1009. In other words, a virtual ink applying position in accordance with the current ink-output position may be superimposed and displayed on an ultrasonic image without depending on the ink-output request signal from the marker. Additionally, it is possible to display both of an ink-applying-position display image generated after actual ink application to a skin surface of an object and a virtual ink-applying-position display image generated before receiving the ink-output request signal in display aspects different from each other.

Next, an ink-applying-position display image will be described.

Figure 22:
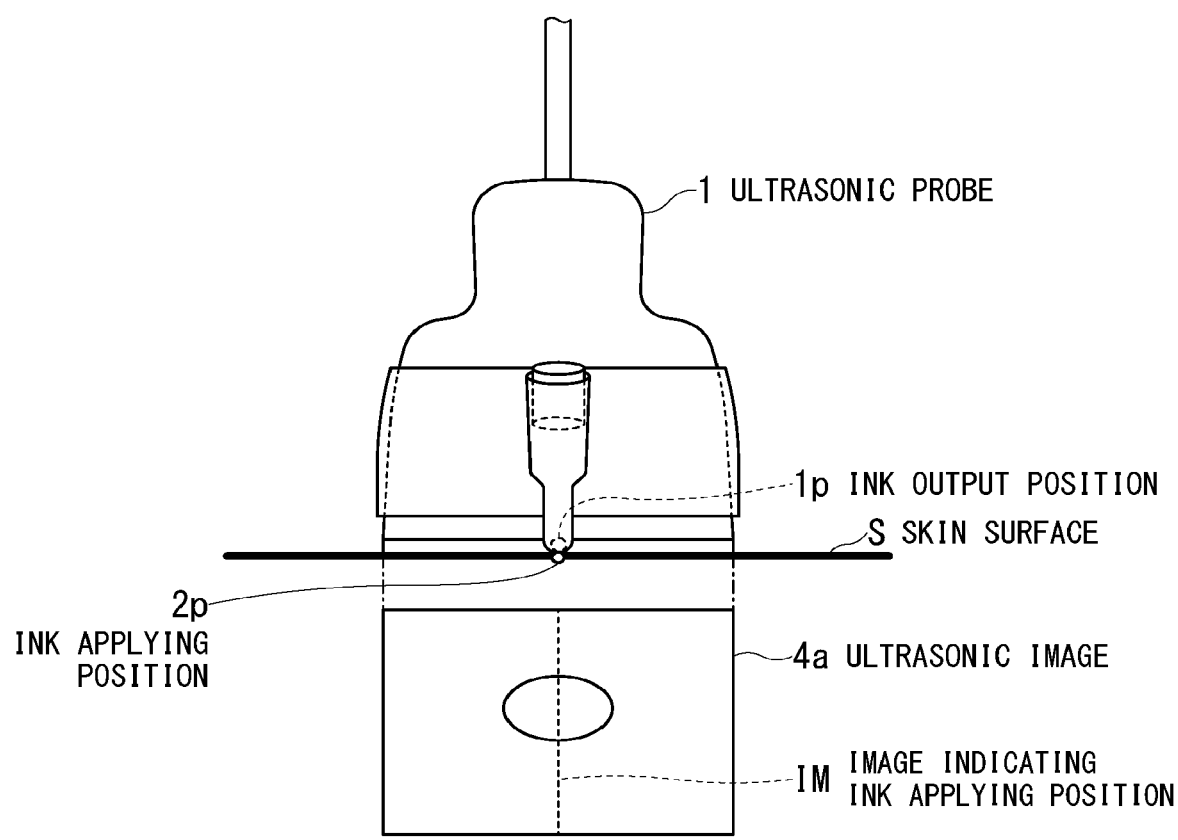
FIG. 22 is the first schematic diagram illustrating an ultrasonic image in the tenth embodiment.

FIG. 22 is the first schematic diagram illustrating an ultrasonic image in the tenth embodiment. FIG. 22 illustrates a case where the ink output position 1*p* is disposed at the center of the front surface of the ultrasonic probe 1. The upper part of FIG. 22 shows a state where the ultrasonic probe 1 is brought into contact with the skin surface S of the object, and the lower part of FIG. 22 shows an ultrasonic image 4*a*. Although the ultrasonic image 4*a* is actually displayed on the monitor 4, the ultrasonic image 4*a* is depicted immediately under the ultrasonic probe 1 in FIG. 22 for easily understanding the correspondence between the ultrasonic probe 1 and the ultrasonic image 4*a*.

FIG. 22 shows the state where ink is applied to the ink applying position 2*p* on the skin surface S of the object from the ink output position 1*p*. As shown by two chain lines in FIG. 22, in the case of a linear probe, both edges of an ultrasonic image positionally match both side surfaces of the ultrasonic probe 1. The ultrasonic image depicts a cross-section under (i.e., deeper than) the skin surface S of the object with which the probe head 1*a* is brought into contact.

In the case of FIG. 22, ink is applied to the ink applying position 2p on the skin surface S of the object from the ink output position 1p immediately beneath the ink output position 1p at the center of the front surface of the ultrasonic probe 1. Thus, the image generation circuit 14 computes the central position of ultrasonic image from the lateral width of the ultrasonic image displayed on the monitor 4 and the length of the ultrasonic probe 1 in the array direction, and causes the monitor 4 to display an image IM indicating the ink applying position at the computed position. In FIG. 22, the dashed straight line indicating the ink applying position is displayed at the center of the ultrasonic image in the depth direction of the ultrasonic image. Note that information such as the lateral width of the ultrasonic image and the length of the ultrasonic probe 1 in the array direction may be stored in the internal memory circuitry 16 or be inputted from outside of the main body 10.

Figure 23:
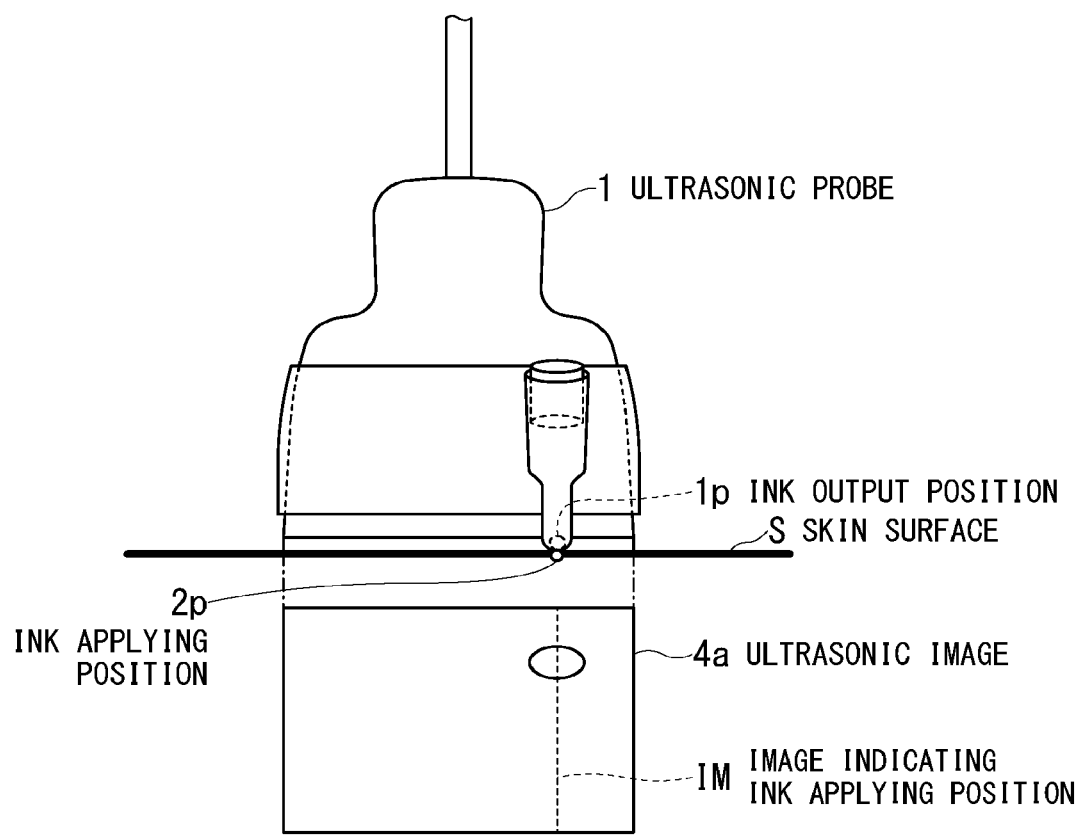
FIG. 23 is the second schematic diagram illustrating an ultrasonic image in the tenth embodiment.

FIG. 23 is the second schematic diagram illustrating an ultrasonic image in the tenth embodiment. FIG. 23 differs from FIG. 22 in that the image IM indicating the ink applying position by a dashed line is displayed on the right side of the ultrasonic image. As described above, the image IM indicating the ink applying position is superimposed and displayed on the ultrasonic image corresponding to the ink applying position 2p on the skin surface S of the object immediately beneath the ink output position 1p.

For instance, when the ink output position 1p shown in FIG. 22 is changed to the ink output position 1p shown in FIG. 23 by manually moving the marker, the ink-applying-position display function 155 may move the ink applying position on the ultrasonic image so that the ink applying position follows the movement of the ink-output position.

Note that an image indicating an ink applying position is not limited to the aspects shown in FIG. 22 and FIG. 23. For instance, an image indicating an ink applying position may be superimposed and displayed by a line or a figure on the upper part or the lower part of an ultrasonic image.

As described above, the same effects as the first embodiment can also be obtained in the tenth embodiment. Further, the ultrasonic diagnostic apparatus 100 of the tenth embodiment superimposes and displays an ink applying position on an ultrasonic image which depicts inside of an object. Thus, a user can easily recognize positional relationship between a skin surface of an object and a target organ or a target tissue. Moreover, it is possible to superimpose and display a virtual ink applying position on an ultrasonic image at a position corresponding to an ink-output position prior to actual ink ejection. In this case, on the basis of the positional relationship between the virtual ink applying position and a target such as an organ and a tissue, a user can apply ink to a desired position such as the position directly on the target and the outline part of the target.

Eleventh Embodiment

In the eleventh embodiment, the ultrasonic diagnostic apparatus 100 analyzes an ultrasonic image and outputs ink based on the analysis result. As an example in the eleventh embodiment, a description will be given of a case where a position of a blood vessel is determined by analyzing an ultrasonic image and ink is applied to the determined position of the blood vessel. Hereinafter, only the difference between the tenth and eleventh embodiments will be described, and duplicate description is omitted.

Figure 24:
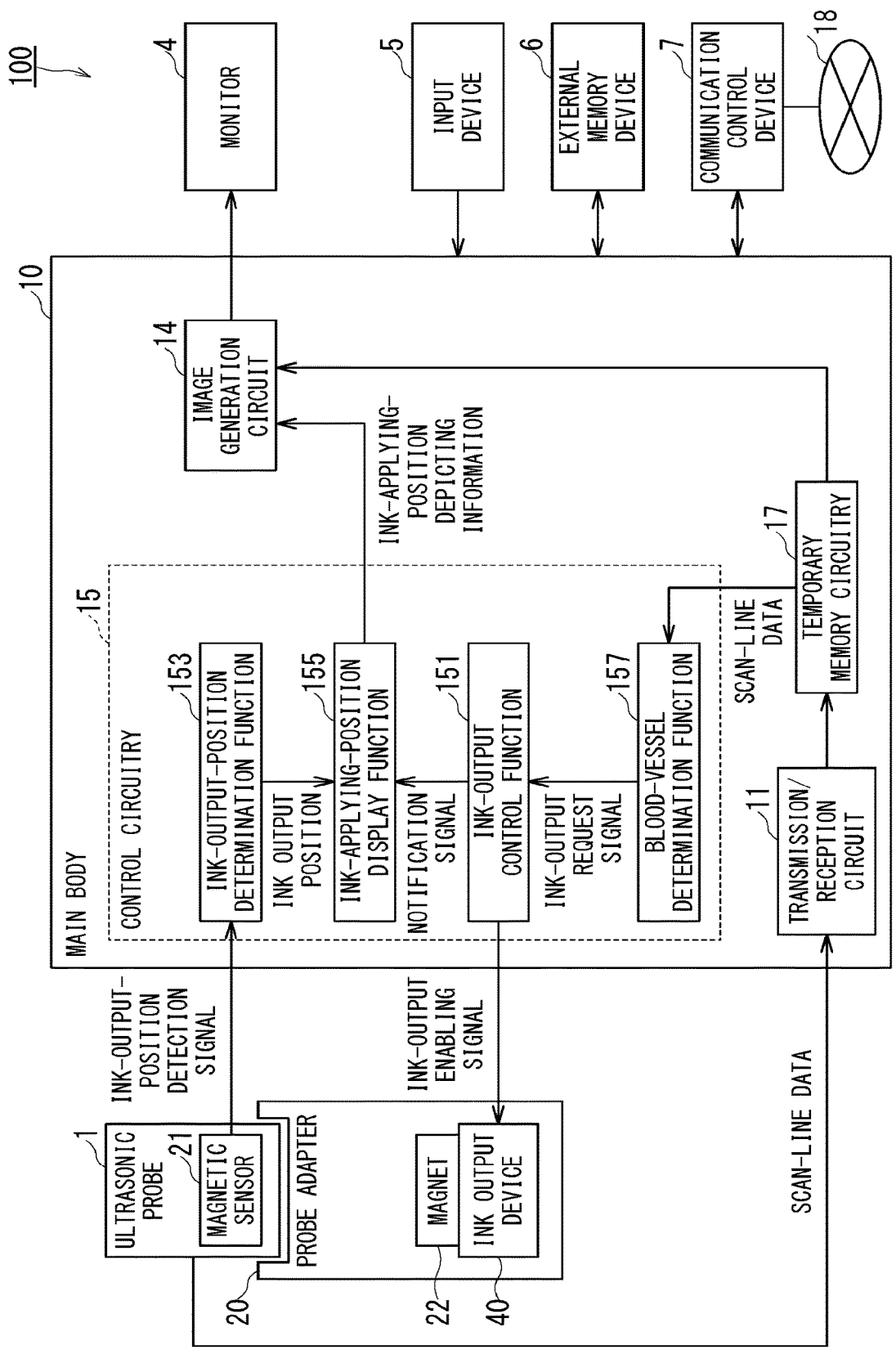
FIG. 24 is a general block diagram illustrating configuration of the ultrasonic diagnostic apparatus of the eleventh embodiment.

FIG. 24 is a general block diagram illustrating configuration of the ultrasonic diagnostic apparatus 100 of the eleventh embodiment. In the eleventh embodiment, the control circuitry 15 of ultrasonic diagnostic apparatus 100 further includes a blood-vessel determination function 157 in addition to the functions of the control circuitry 15 in the tenth embodiment shown in FIG. 19.

The blood-vessel determination function 157 is a function of determining whether a blood vessel exists at the ink-output position or not, on the basis of at least one set of scan-line data. When a blood vessel exists at the ink-output position, the ink-output request signal is transmitted from the blood-vessel determination function 157 to the ink-output control function 151.

Figure 25:
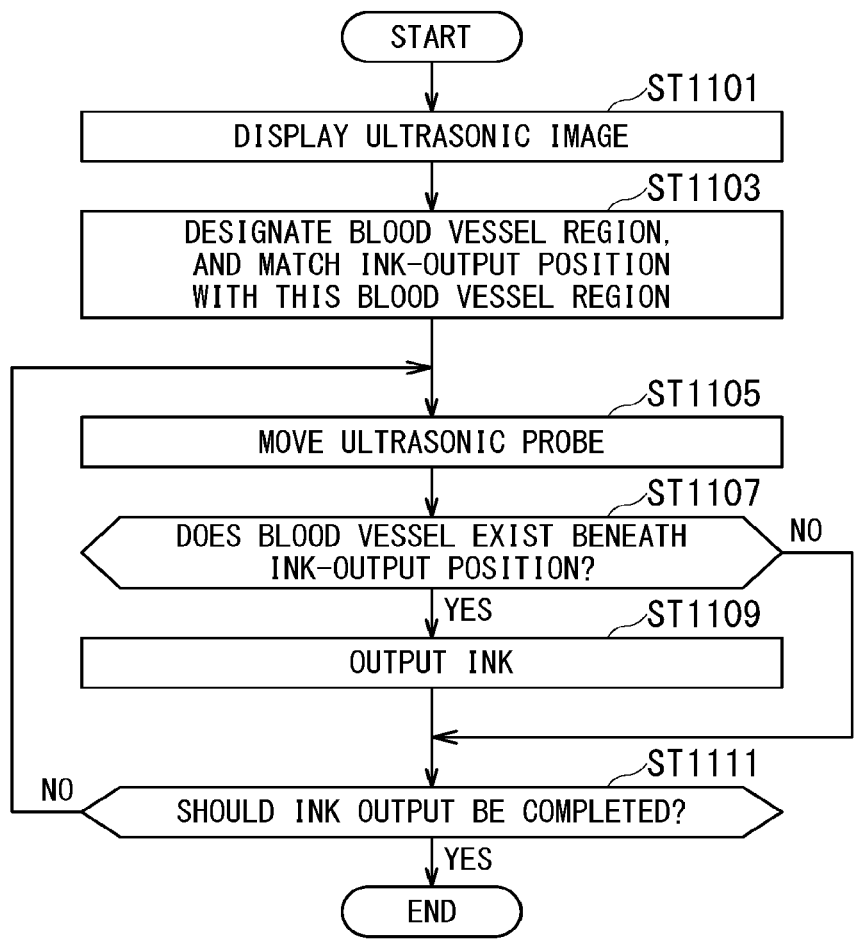
FIG. 25 is a flowchart illustrating an operation performed by the ultrasonic diagnostic apparatus of the eleventh embodiment.

FIG. 25 is a flowchart illustrating an operation performed by the ultrasonic diagnostic apparatus 100 of the eleventh embodiment.

In the step ST1101, the monitor 4 displays an ultrasonic image. The monitor 4 may superimpose a virtual ink applying position on the displayed ultrasonic image, under the premise that ink is applied to a skin surface of an object from the current ink-output position.

In the step ST1103, a user designates a blood vessel region displayed on the ultrasonic image, and matches the ink-output position with the blood vessel region. A user moves the ultrasonic probe 1 or the marker in the array direction in such a manner that the blood vessel is located beneath the ink-output position. In this operation, a user can use the ink applying position virtually displayed on the monitor 4 as a guide. As described above, a user designates a marking start position of a blood vessel which is a marking target, and causes the ink output device 40 to eject ink by pressing the button for ink output.

In the step ST1105, a user moves the ultrasonic probe 1 along the running direction of the blood vessel.

In the next step ST1107, the blood-vessel determination function 157 determines whether a blood vessel exists under the ink-output position in a frame or not.

Here, number of ultrasonic images which the ultrasonic diagnostic apparatus 100 can generate per second is referred to as frame number or frame rate, and each of time-sequential ultrasonic images to be generated in accordance with this frame rate is defined as a frame. The ultrasonic diagnostic apparatus 100 generates plural ultrasonic images in accordance with the frame rate as time-sequential frames, and controls the monitor 4 such that the updated frame is sequentially displayed on the monitor 4. As to determination on presence/absence of a blood vessel at the ink-output position, the blood-vessel determination function 157 may reduce computation burden by analyzing scan-line data of a predetermined ratio of all the frames so as to securely follow the frame rate (i.e., real-time image generation) as an example here. As to the method of determining blood vessel by the blood-vessel determination function 157, it will be described below in detail by referring to FIG. 26.

When the blood-vessel determination function 157 determines that a blood vessel exists at the ink-output position, the processing proceeds to the step ST1109. Conversely, when the blood-vessel determination function 157 determines that a blood vessel does not exist at the ink-output position, the processing proceeds to the step ST1111 without going through the step ST1109.

In the step ST1109, the ink-output control function 151 transmits the ink-output enabling signal to the ink output device 40. The ink output device 40 applies ink to a skin surface of an object in response to the ink-output enabling signal.

In the step ST1111, the control circuitry 15 determines whether marking should be completed or not. When it is determined that marking should be continued, the processing returns to the step ST1105 and the processing of the steps ST1105 to ST1111 is repeated. When it is determined that marking should be completed, ending processing is performed to complete marking.

Figure 26:
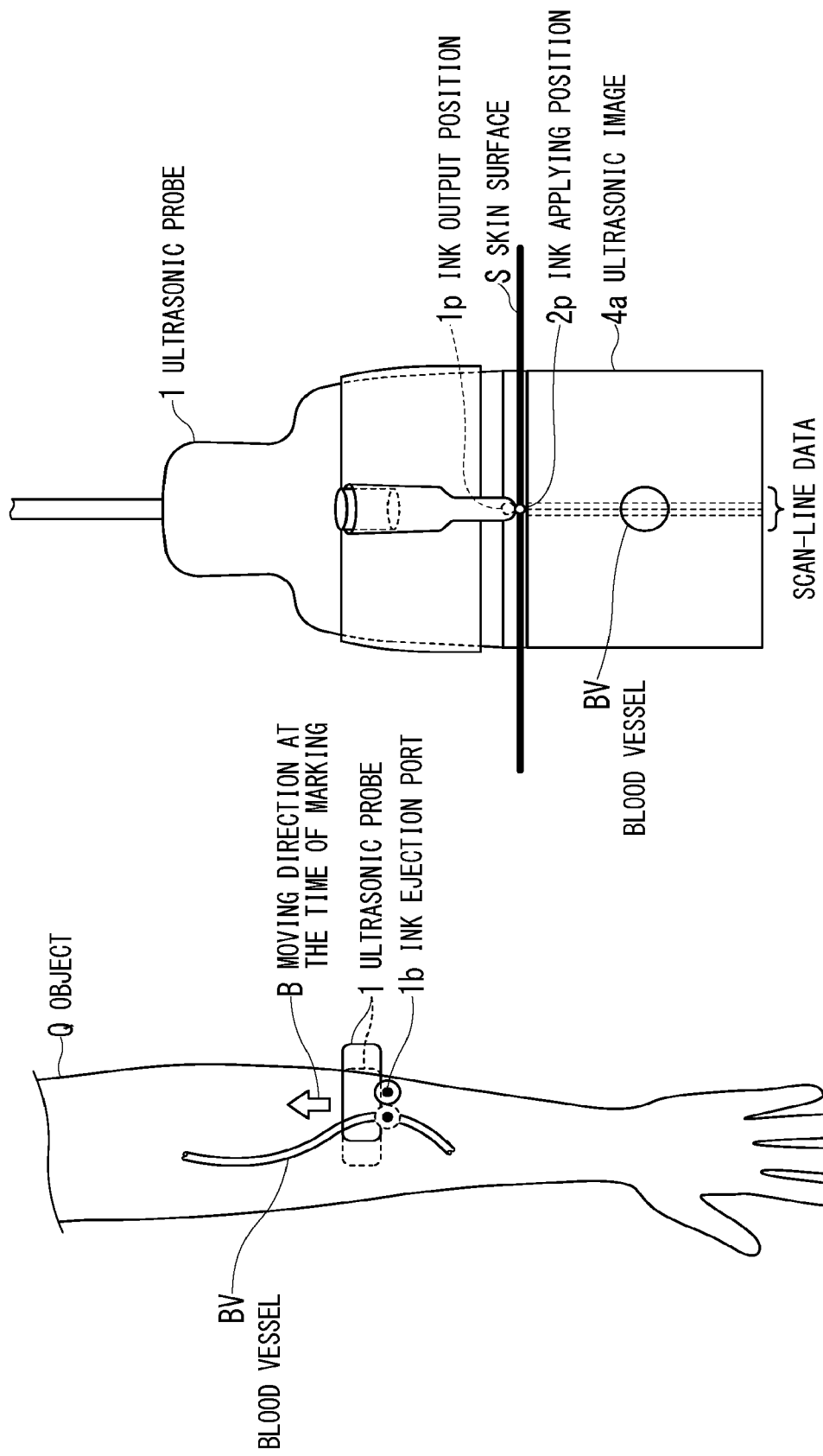
FIG. 26 is a schematic diagram illustrating a method of identifying a blood vessel with the use of the ultrasonic diagnostic apparatus of the eleventh embodiment.

FIG. 26 is a schematic diagram illustrating a method of identifying a blood vessel with the use of the ultrasonic diagnostic apparatus 100 of the eleventh embodiment. FIG. 26 illustrates a case where a running state of a blood vessel in the arm of the object Q is marked by using the ultrasonic diagnostic apparatus 100. The left side of FIG. 26 shows the state in which the ultrasonic probe 1 is brought into contact with the marking start position of the blood vessel BV in the arm of the object Q. The upper part of the right side of FIG. 26 shows the state in which the ultrasonic probe 1 is brought into contact with the skin surface S of the object Q, similarly to FIG. 22 and FIG. 23. The lower part of the right side of FIG. 26 shows the ultrasonic image 4a.

In the left side of FIG. 26, the blood vessel BV does not exist immediately beneath the ink output position 1p of the ultrasonic probe 1 indicated by a circular solid line. Thus, a user moves the ultrasonic probe 1 in the array direction from the position indicated by the solid-line to the position indicated by the dashed-line.

As shown in FIG. 26, when the ultrasonic probe 1 is brought into contact with the skin surface S such that the array direction of the ultrasonic probe 1 is in parallel with the short axis direction of the blood vessel BV of the object Q, a short-axis view of the blood vessel By is depicted in each of ultrasonic images to be acquired. A user moves the ultrasonic probe 1 in the array direction so as to locate the ink-output position 1p above the short-axis view of the blood vessel BV of the marking target, while observing each frame (i.e., ultrasonic image). The right side of FIG. 26 shows the state after the position of the ultrasonic probe 1 is adjusted such that the ink-output position 1p is located above the short-axis view of the blood vessel BV of the marking target.

When the marking start position is determined in the above manner, a user moves the ultrasonic probe 1 in the direction of the arrow B shown on the left side of FIG. 26. The ultrasonic diagnostic apparatus 100 generates plural frames per second, and the blood-vessel determination function 157 determines whether a blood vessel exists at the ink output position 1p or not, for each of predetermined ratio of all the generated frame.

The blood-vessel determination function 157 determines presence/absence of a blood vessel on the basis of scan-line data corresponding to the ink output position 1p. Data of one frame are composed of plural scan-line data, and the blood-vessel determination function 157 determines whether a blood vessel exists immediately beneath the ink output position 1p or not, on the basis of at least one set of scan-line data. The right side of FIG. 26 shows a case where presence/absence of a blood vessel is determined by using three lines of scan-line data.

The ultrasonic diagnostic apparatus 100 causes the monitor 4 to display cross-sectional images by converting change in signal intensity of a reception signal, which is a reflected wave, into brightness (luminance) and generating image based on the converted brightness. When an ultrasonic wave transmitted from the ultrasonic probe 1 travels inside a living body, the larger difference in acoustic impedance between tissues is, the larger the signal intensity of the reception signal becomes. Conversely, when difference in acoustic impedance is small, an ultrasonic wave does not reflect so much and increases in amount of penetrating through the living body. Inside of a blood vessel is generally filled with blood, and difference in acoustic impedance is not generated so much in the running region of blood. Thus, in a cross-sectional ultrasonic image, a blood vessel is depicted as a region of plural low-brightness pixels adjacent to each other.

Specifically, a user designates a target region to be tracked (i.e., traced) inside the blood vessel by using the input device 5. The blood-vessel determination function 157 extracts data sets in the range of the designated depth from at least two sets of scan-line data in the first frame on which the user designated a region inside a blood vessel, which scan-line data are inside the blood vessel and correspond to the ink output position 1p existing within the range inside the blood vessel designated by a user. Note that scan-line data are subjected to attenuation of approximately 0. 3 db/cm/MHz in the depth direction in the case of a uniform soft tissue, the extracted scan-line data are corrected by the following formula (1).

$$\text{Scan-Line Dara after Correction} = \quad (1)$$
$$(\text{Scan-Line Data before Correction}) \times$$
$$\left(10^{\frac{0.3}{20} \times Center\ Frequency\ (MHz) \times Depth\ (cm)}\right)$$

Afterward, the blood-vessel determination function 157 computes an average value and a standard deviation for the extracted data sets in the range of the designated depth, and computes the range defined by the formula (2).

$$(\text{Average Value}) \pm k^* (\text{Standard Deviation}) \quad (2)$$

The constant k in the formula (2) is a coverage factor which is statistically determined on the basis of sampling number of data sets designated as an area inside the blood vessel by a user.

The blood-vessel determination function 157 newly computes an average value and a standard deviation for scan-line data of the second frame in the range designated by a user in a similar manner as described above. When the average value computed for the scan-line data of the second frame is within the range obtained by applying the formula (2) to the average value and the standard deviation of the previous frame (i.e., the first frame), the blood-vessel determination function 157 can determine that a blood vessel region exists in the second frame at the same position as the position of the blood vessel in the first frame. Similarly, when the average value computed for the third frame is within the range obtained by applying the formula (2) to the average value and the standard deviation of the second frame, the blood-vessel determination function 157 can determine that a blood vessel region exists in the third frame at the same position as the position of the blood vessel in the second frame. By repeating the above-described processing, the blood-vessel determination function 157 continues to determine whether a blood vessel exists at the ink output position 1p or not.

The blood-vessel determination function 157 identifies an existence region of a blood vessel based on the above-described processing. Since the blood vessel BV shown in FIG. 26 is curved rightward, the ink output position 1p does not pass on the blood vessel when the ultrasonic probe 1 is moved from the marking start position in the direction of the arrow B.

When the blood-vessel determination function 157 determines that the ink output position 1p has deviated from the blood vessel BV, the monitor 4 to display textual information and/or image which warn that the ink output position $1p$ has deviated from the blood vessel BV. Additionally, when the ink output position $1p$ has deviated from the blood vessel BV, a user moves the ultrasonic probe 1 or the ink output position $1p$ in such a manner that the ink output position $1p$ is located above the blood vessel BV again. In this operation, a user moves the ultrasonic probe 1 in the array direction. The above-described processing of determining presence/absence of a blood vessel is sequentially performed for each updated frame, and ink is automatically outputted when the blood-vessel determination function 157 determines again that a blood vessel exists immediately beneath the ink output position $1p$. Further, the monitor 4 to display information that the ink output position $1p$ has returned to the position above the blood vessel BV again.

Although ink is outputted when the blood vessel BV exists immediately beneath the ink output position $1p$ in the eleventh embodiment, a condition of ink output is not limited to the above-described aspect. For instance, ink output may be started at the timing of determining the marking start position at the beginning, and the ink-output stop signal may be outputted to the circuit region of the ink-output control function 151 in the control circuitry 15 when the control circuitry 15 determines that the blood vessel BV does not exist immediately beneath the ink output position $1p$ according to its blood-vessel determination function 157.

Additionally, the ultrasonic diagnostic apparatus 100 may be configured such that ink is outputted in a period during which the ink output position $1p$ is located above the position of the blood vessel BV. In this configuration, ink is applied to a skin surface of an object only in each period during which the ink output position $1p$ is located above the position of the blood vessel BV, and marking can be intermittently performed by moving the ultrasonic probe 1 to a running region of a blood vessel even when the position of the ink output position $1p$ is deviated from the position of the blood vessel BV.

Further, a user can perform continuous marking by moving the ultrasonic probe 1 on a skin surface of an object while shifting the position of the ink output position $1p$. Specifically, the ultrasonic probe 1 is moved in the direction of the arrow B in FIG. 26 such that the running region of the target blood vessel to be marked is included, and then the ultrasonic probe 1 is moved in the array direction. In this case, ink is applied to a skin surface of an object only when the blood vessel exists immediately beneath the ink output position $1p$. By moving the ultrasonic probe 1 in the direction of the arrow B in FIG. 26 again, ink is applied to the skin surface of the object only when the blood vessel exists immediately beneath the ink output position $1p$. A user can mark the entire running region of the target blood vessel by gradually moving the ultrasonic probe 1 along the running region of the target blood vessel while alternately repeating the manipulation of moving the ultrasonic probe 1 in the array direction and the manipulation of moving the ultrasonic probe 1 in the direction perpendicular to the array direction.

Although a description has been given of the case where a marking target is a blood vessel in the eleventh embodiment, the control circuitry 15 may be configured to treat another structure, which can be a treatment target such as an organ or a tumor, as a marking target.

In the eleventh embodiment, a description has been given of the case where the ink applying position $2p$ is determined from the scan-line data acquired by the ultrasonic diagnostic apparatus 100. However, a method of determining the ink applying position $2p$ is not limited to a method of using scan-line data. The ink applying position $2p$ may be determined by performing positional matching between an ultrasonic image and a medical image generated by another modality such as an X-ray CT (Computed Tomography) image and an MR (Magnetic Resonance) image.

For instance, there is a known technology in which an ultrasonic image is aligned with another medical image generated by another modality such as an X-ray CT image and an MR image and then both images are displayed in parallel on a display of an ultrasonic diagnostic apparatus. A scanning operation using an ultrasonic wave can be performed in conjunction with display of an X-ray CT image (or MR image) by installing a magnetic position sensor on the ultrasonic probe and matching the inspection position in the ultrasonic image detected by this magnetic position sensor with the cross-section of this X-ray CT image (or MR image). Since conventional technology can be applied to positional matching between an ultrasonic image and an X-ray CT image (or MR image) and can be applied to display in conjunction with scanning, their detailed descriptions are omitted. Note that the ultrasonic diagnostic apparatus 100 acquires a medical image generated by another modality via the electronic network 18. Medical images are stored in an image server such as PACS (Picture Archiving and Communication Systems).

When a position and/or a shape of structure of the treatment target such as a blood vessel and a tumor is identified in a medical image generated by another modality, the ink applying position $2p$ can be determined on the basis of the position of the structure identified on this medical image by aligning this medical image and an ultrasonic image with the use of the above-described positional matching technology. In other words, the ultrasonic diagnostic apparatus 100 may be configured such that the ink applying position $2p$ (i.e., target position of ink application) is previously identified on the medical image and ink is outputted when the ink applying position $2p$ identified on the medical image matches the ink output position $1p$ of the marker provided on the ultrasonic probe 1 moving on the surface of the object. The above-described "previously" means to be prior to marking the object depicted in the medical image by using the ultrasonic diagnostic apparatus.

For instance, in the case of a blood vessel, a user previously identifies the treatment-target vessel (i.e., target blood vessel to be treated) on a medical image such as an X-ray CT image, and inputs information on the treatment target position such as the start position and the range of the treatment-target vessel, wherein "previously" means the same as described above. Next, positional matching is performed between an ultrasonic image and the X-ray CT image which is associated with the information on the treatment target, and the X-ray CT image is displayed so as to follow the scanning operation using an ultrasonic wave. On the ultrasonic image displayed on the monitor 4, the ink output position $1p$ indicative of the position of the marker provided on the ultrasonic probe 1 is superimposed and displayed on the basis of information detected by a magnetic sensor and a magnetic position sensor. When the ink output position $1p$ matches the treatment target position identified on the X-ray CT image (i.e., the target position of ink application) after movement of the ultrasonic probe 1 operated by a user, ink is outputted from the marker.

As described above, at the timing when positional matching between the ultrasonic image and the X-ray CT image is completed, the ink applying position $2p$ is identified. Thus, on the basis of the identified ink applying position $2p$ and the current ink output position 1p, the control circuitry 15 may cause the monitor 4 to display in which direction the ultrasonic probe 1 should be moved. For instance, in the case of an echo signal from a lower limb, the control circuitry 15 may cause the monitor 4 to display a schematic diagram of the lower limb of the object and to superimpose the current probe position and the moving target position of the ultrasonic probe 1 on the displayed schematic diagram. In this superimposed display, the current probe position (i.e., ink output position 1p) and the moving target position of the ultrasonic probe 1 (i.e., the target position of ink application) may be indicated by marks different from each other such as a circle and a triangle. Further, when a user observes the blood vessel in the long-axis direction, the control circuitry 15 may cause the monitor 4 to display both of the ink output position 1p indicative of the current position of the ultrasonic probe 1a and a figure such as an arrow indicative of the direction in which the target position exists. In such configuration, a user can easily identify the appropriate moving direction of the ultrasonic probe 1.

As described above, the ultrasonic diagnostic apparatus 100 maybe configured to identify a treatment target on a medical image excluding an ultrasonic image and to apply ink when the ultrasonic probe 1 is moved to the position above the skin surface of the object where the treatment target exists. For instance, the ultrasonic diagnostic apparatus 100 may be configured to apply ink at the timing when the position closest to the start position of the treatment target blood vessel is scanned by the ultrasonic probe 1. Additionally, the ultrasonic diagnostic apparatus 100 may be configured to identify a position of a treatment-target vessel closest to a skin surface on an X-ray CT image as a treatment target position and to apply ink to this treatment target position.

Note that the position of the treatment-target vessel closest to the skin surface may be identified from ultrasonic image data. In other words, the ultrasonic diagnostic apparatus 100 may be configured to measure distance between the treatment target blood identified on a medical image and the bottom surface of the ultrasonic probe 1 (i.e., the skin surface S) each time of transmitting an ultrasonic wave for scanning the object and to apply ink to a position where the measured distance is below an arbitrary threshold value. Here, the above-described position closest to the skin surface is, e.g., the position of the ultrasonic probe 1 which gives the smallest distance between the bottom surface of the ultrasonic probe 1 attached to the object (i.e., the skin surface S) and the position of the blood vessel shallowest from the skin surface S.

As described above, by using a medical image generated by another modality, it is possible to determinate the ink applying position 2p with the use of information which cannot be acquired by the ultrasonic diagnostic apparatus 100. For instance, even when a blood flow does not exists due to an occluded blood vessel, it is possible to identify the shape and the position of this blood vessel in detail by using the result obtained by analyzing a medical image which is generated by another modality.

Additionally, when a user hopes to perform marking in the long-axis direction of a blood vessel, a user can easily perform marking by identifying the marking start position and moving the ultrasonic probe in the running direction of the blood vessel. This is because the marking start position can be previously identified on the medical image and thus the marking start position can be easily identified by displaying the ultrasonic image and the medical image in conjunction with each other. Further, when the marking end position is specified on the medical image, a user can perform marking on a desired range by moving the ultrasonic probe 1 along the running direction of the blood vessel.

Moreover, the ink output position 1p is superimposed and displayed on an ultrasonic image, and it is possible by displaying letters and/or an image or outputting sound to inform a user of the fact that ink is actually applied to the skin surface of the object. In other words, a user can apply ink to a desired position (i.e., ink applying position 2p) only by scanning the part of the object around the ink applying position 2p with the ultrasonic probe 1.

As described above, the same effects as the first embodiment can also be obtained in the eleventh embodiment. Further, in the eleventh embodiment, it is possible to analyze an ultrasonic image and automatically output ink in accordance with the analysis result.

According to the probe adapter 20, the ultrasonic probe 1, and the ultrasonic diagnostic apparatus 100 of at least one of the above-described embodiments, it is possible to operate the ultrasonic probe 1 with one hand at the time of marking, and efficiency of a marking operation and marking accuracy can be improved.

Correspondences between terms used in the claims and terms used in the embodiments will be described. Note that the correspondences described below are just some of possible interpretations for reference and should not be construed as limiting the present invention.

In FIG. 3, the central two transducers which are shorter in the elevation direction than the rest are examples of the first transducer recited in the claims, and the rest of the transducers are examples of the second transducers recited in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A probe adapter comprising:
    a holder configured to be detachably attached to an ultrasonic probe;
    a marker disposed at a predetermined position on the ultrasonic probe in an array direction in which transducers are arrayed, the marker being configured to mark a surface of an object which the ultrasonic probe is brought into contact with, under a state where the holder is attached to the ultrasonic probe; and
    a wiper configured to remove an ultrasonic medium coated on the surface of the object, wherein
    the wiper includes an angle adjuster configured to adjust an angle between the ultrasonic probe and the marker in such a manner that the wiper is kept in contact with the surface of the object.

2. The probe adapter according to claim 1,
    wherein the marker is configured to be equipped with a button and mark the surface of the object in accordance with pressing-down of the button.

3. The probe adapter according to claim 1, further comprising an adjuster configured to
    adjust a position of the marker by bringing a tip of the marker into contact with the surface of the object when marking is performed by the marker, and adjust a position of the marker by separating the tip of the marker from the surface of the object when marking is not performed by the marker.

4. The probe adapter according to claim 1,
wherein the wiper is configured to
be slidably provided with respect to the holder,
slide toward a side of the surface of the object when marking is performed, and
slide in a direction away from the surface of the object when marking is not performed.

5. The probe adapter according to claim 1,
wherein the marker is configured to mark the surface of the object with at least one of ink, a marking pen, and an ink head.

6. The probe adapter according to claim 1,
wherein the marker is configured to be mounted on the holder such that the marker is slidable in parallel with the surface of the object when the surface of the object is scanned by the ultrasonic probe with the holder attached to the ultrasonic probe.

7. An ultrasonic diagnostic apparatus comprising:
(a) an ultrasonic probe;
(b) the probe adapter as recited in claim 1;
(c) processing circuitry configured to generate an ultrasonic image based on a reception signal outputted from the ultrasonic probe;
(d) memory circuitry configured to store a marking position on the surface of the object to be marked by the marker; and
(e) a monitor configured to superimpose and display the marking position on the ultrasonic image.

8. The ultrasonic diagnostic apparatus according to claim 7, the processing circuitry configured to
determine presence/absence of a target structure at the marking position based on a part of a reflected wave from the object, the reflected wave being detected by the ultrasonic probe, and
determine whether marking is performed on the surface of the object or not, in accordance with a determination result of the presence/absence of a target structure at the marking position.

9. The ultrasonic diagnostic apparatus according to claim 7,
wherein the processing circuitry is configured to cause the marker to move in parallel with the surface of the object to a position where the target structure exists, when the target structure does not exist at the marking position.

10. The ultrasonic diagnostic apparatus according to claim 8,
wherein the target structure includes a blood vessel, a tumor, or an organ.

11. The ultrasonic diagnostic apparatus according to claim 8,
wherein the processing circuitry is configured to determine whether marking is performed on the surface of the object or not, based on an ink-output request signal from the marker.

12. The ultrasonic diagnostic apparatus according to claim 7,
wherein the ultrasonic probe is equipped with a magnetic sensor;
the marker is equipped with a magnet; and
the magnetic sensor is configured to detect a position of the magnet and detect the marking position based on the position of the magnet.

13. The ultrasonic diagnostic apparatus according to claim 8,
wherein the ultrasonic probe is equipped with a magnetic sensor;
the marker is equipped with a magnet; and
the magnetic sensor is configured to detect a position of the magnet and detect the marking position based on the position of the magnet.

14. The ultrasonic diagnostic apparatus according to claim 8,
wherein the ultrasonic probe is equipped with a magnetic sensor;
the marker is equipped with a magnet; and
the magnetic sensor is configured to detect a position of the magnet and detect the marking position based on the position of the magnet.

15. The ultrasonic diagnostic apparatus according to claim 7,
wherein the ultrasonic probe further includes a magnetic position sensor configured to detect a detection position of the ultrasonic probe; and
the processing circuitry is configured to
align an ultrasonic image acquired at the detection position of the ultrasonic probe and a medical image generated by another modality,
determine presence/absence of the target structure at the marking position based on the medical image which is aligned with the ultrasonic image, and
determine whether marking is performed on the surface of the object or not, in accordance with a determination result of the presence/absence of the target structure at the marking position.

16. A probe adapter comprising:
a holder configured to be detachably attached to an ultrasonic probe;
a marker disposed at a predetermined position on the ultrasonic probe in an array direction in which transducers are arrayed, the marker being configured to mark a surface of an object which the ultrasonic probe is brought into contact with, under a state where the holder is attached to the ultrasonic probe; and
a wiper configured to remove an ultrasonic medium coated on the surface of the object, wherein
the wiper is configured to
be slidably provided with respect to the holder,
slide toward a side of the surface of the object when marking is performed, and
slide in a direction away from the surface of the object when marking is not performed.

17. The probe adapter according to claim 16,
wherein the marker is configured to be equipped with a button and mark the surface of the object in accordance with pressing-down of the button.

18. The probe adapter according to claim 16, further comprising an adjuster configured to
adjust a position of the marker by bringing a tip of the marker into contact with the surface of the object when marking is performed by the marker, and
adjust a position of the marker by separating the tip of the marker from the surface of the object when marking is not performed by the marker.

19. The probe adapter according to claim 16,
wherein the marker is configured to mark the surface of the object with at least one of ink, a marking pen, and an ink head.

20. The probe adapter according to claim 16,
wherein the marker is configured to be mounted on the holder such that the marker is slidable in parallel with the surface of the object when the surface of the object is scanned by the ultrasonic probe with the holder attached to the ultrasonic probe.

* * * * *